United States Patent
Ohashi

(10) Patent No.: US 11,298,098 B2
(45) Date of Patent: Apr. 12, 2022

(54) X-RAY DIAGNOSIS APPARATUS AND IMAGE PROCESSING METHOD

(71) Applicant: CANON MEDICAL SYSTEMS CORPORATION, Otawara (JP)

(72) Inventor: Shumpei Ohashi, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 74 days.

(21) Appl. No.: 16/582,090

(22) Filed: Sep. 25, 2019

(65) Prior Publication Data

US 2020/0113535 A1 Apr. 16, 2020

(30) Foreign Application Priority Data

Sep. 25, 2018 (JP) .............. JP2018-178341
Sep. 25, 2019 (JP) .............. JP2019-174031

(51) Int. Cl.
*A61B 6/00* (2006.01)

(52) U.S. Cl.
CPC ............ *A61B 6/542* (2013.01); *A61B 6/4441* (2013.01); *A61B 6/463* (2013.01); *A61B 6/486* (2013.01); *A61B 6/488* (2013.01)

(58) Field of Classification Search
CPC .......... A61B 6/00; A61B 6/542; A61B 6/463; A61B 6/4441; A61B 6/488; A61B 6/486; A61B 6/102; A61B 6/487; A61B 6/5235; A61B 6/06; A61B 6/5241
See application file for complete search history.

(56) References Cited

U.S. PATENT DOCUMENTS 9,480,437 B2* 11/2016 Watanabe .............. A61B 6/022
2013/0101084 A1 4/2013 Shimizu
2015/0078524 A1 3/2015 Shimizu

FOREIGN PATENT DOCUMENTS

JP 2013-090912 A 5/2013

* cited by examiner

*Primary Examiner* — Jurie Yun
(74) *Attorney, Agent, or Firm* — Oblon, McClelland, Maier & Neustadt, L.L.P.

(57) ABSTRACT

An X-ray diagnosis apparatus according to an embodiment includes: processing circuitry configured: to sequentially generate X-ray image data based on a detection result obtained by an X-ray detector; to specify a radiation region of X-rays in each piece of X-ray image data generated during the move of an X-ray blocking member that is moved by an X-ray limiting device on the basis of an operation received by an input interface; to sequentially generate, during the move of the X-ray blocking member, first combined image data by using the radiation region, by combining first X-ray image data generated during the move of the X-ray blocking member, with second X-ray image data generated prior to the move of the X-ray blocking member and stored in storage circuitry; and to cause a display to display a combined image represented by the first combined image data.

20 Claims, 15 Drawing Sheets

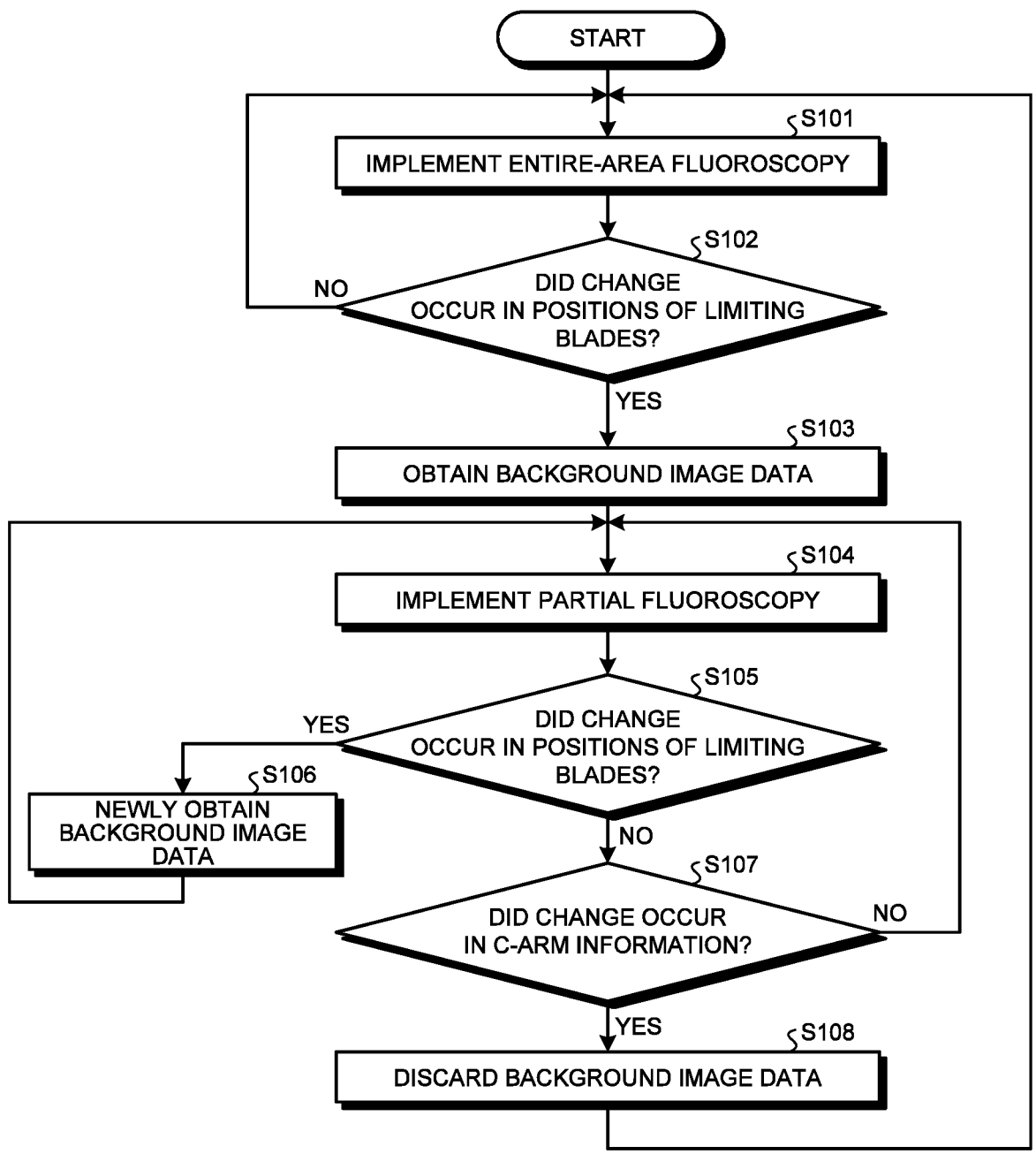

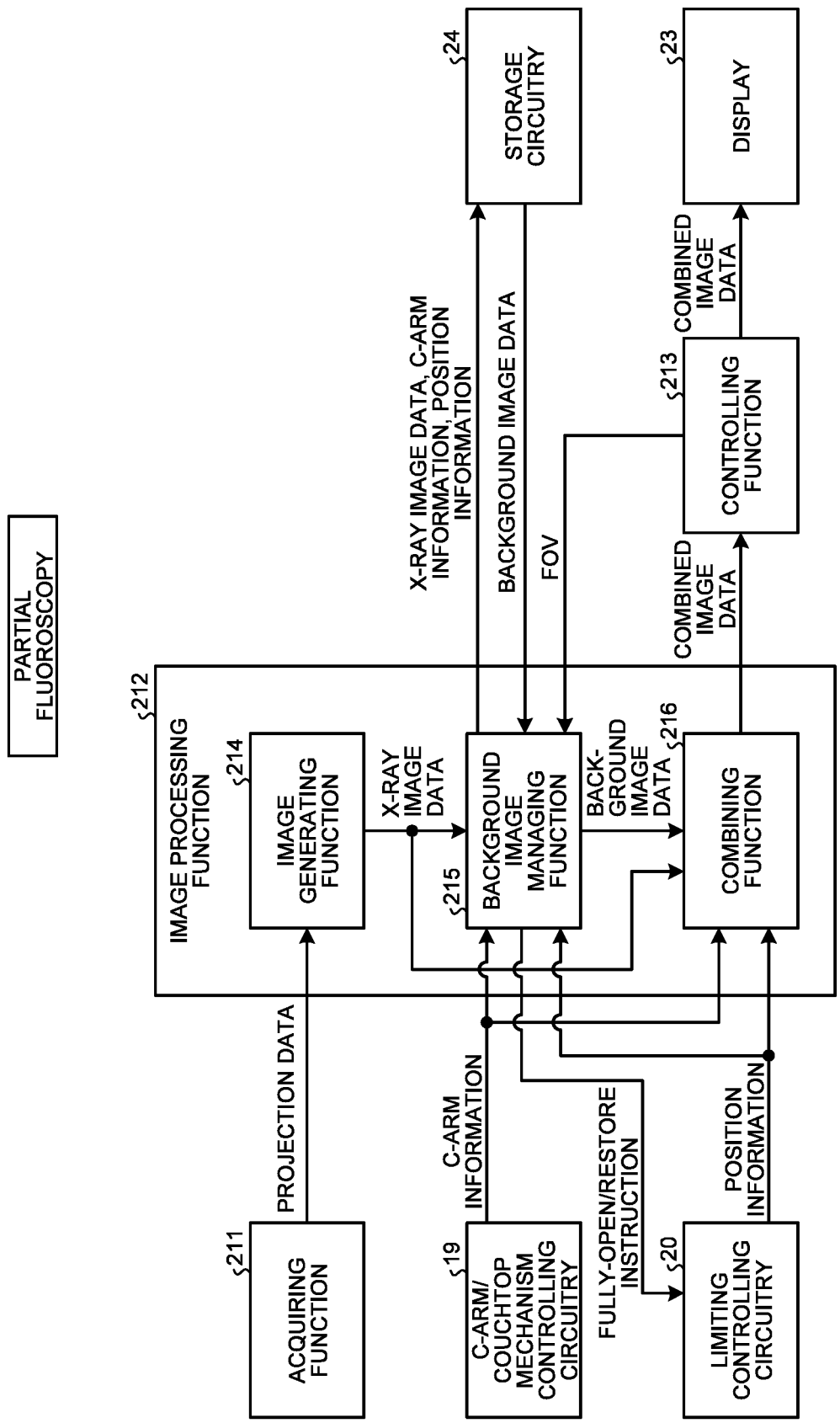

X-RAY DIAGNOSIS APPARATUS AND IMAGE PROCESSING METHOD

CROSS-REFERENCE TO RELATED APPLICATIONS

This application is based upon and claims the benefit of priority from Japanese Patent Application No. 2018-178341, filed on Sep. 25, 2018 and Japanese Patent Application No. 2019-174031, filed on Sep. 25, 2019; the entire contents of which are incorporated herein by reference.

FIELD

Embodiments described herein relate generally to an X-ray diagnosis apparatus and an image processing method.

BACKGROUND

There are techniques for reducing radiation exposure for examined subjects and practitioners during implementation of various types of manipulations such as ablation manipulations. For instance, examples of the techniques used for reducing the radiation exposure include a technique called partial fluoroscopy. For example, partial fluoroscopy is fluoroscopy by which a real-time image is displayed on the inside of a Region Of Interest (ROI), while a background image (a past image) is displayed on the outside thereof.

BRIEF DESCRIPTION OF THE DRAWINGS

FIG. 8 is a flowchart for explaining an example of a flow in the processes performed by the X-ray diagnosis apparatus according to the first embodiment;

FIG. 9 is a chart for explaining an example of processes performed by an X-ray diagnosis apparatus according to a first modification example of the first embodiment;

DETAILED DESCRIPTION

An X-ray diagnosis apparatus according to an embodiment includes an X-ray detector, storage circuitry, an X-ray limiting device, an input interface, and processing circuitry. The X-ray detector is configured to detect X-rays emitted from an X-ray tube. The storage circuitry is configured to store therein X-ray image data sequentially generated on the basis of a detection result obtained by the X-ray detector. The X-ray limiting device includes a movable X-ray blocking member and is configured to restrict a range radiated with the X-rays emitted from the X-ray tube. The input interface is configured to receive an operation to move the X-ray blocking member. The processing circuitry is configured to sequentially generate the X-ray image data based on the detection result obtained by the X-ray detector. The processing circuitry is configured to specify a radiation region of the X-rays in each piece of X-ray image data generated during the move of the X-ray blocking member that is moved by the X-ray limiting device on the basis of the operation received by the input interface. The processing circuitry is configured to sequentially generate, during the move of the X-ray blocking member, first combined image data by using the radiation region, by combining first X-ray image data generated during the move of the X-ray blocking member, with second X-ray image data generated prior to the move of the X-ray blocking member and stored in the storage circuitry. The processing circuitry is configured to cause a display to sequentially display combined images represented by the first combined image data.

Exemplary embodiments of an X-ray diagnosis apparatus and an image processing method will be explained in detail below, with reference to the accompanying drawings. The X-ray diagnosis apparatus and the image processing method of the present disclosure are not limited to the embodiments described below.

First Embodiment

Figure 1:
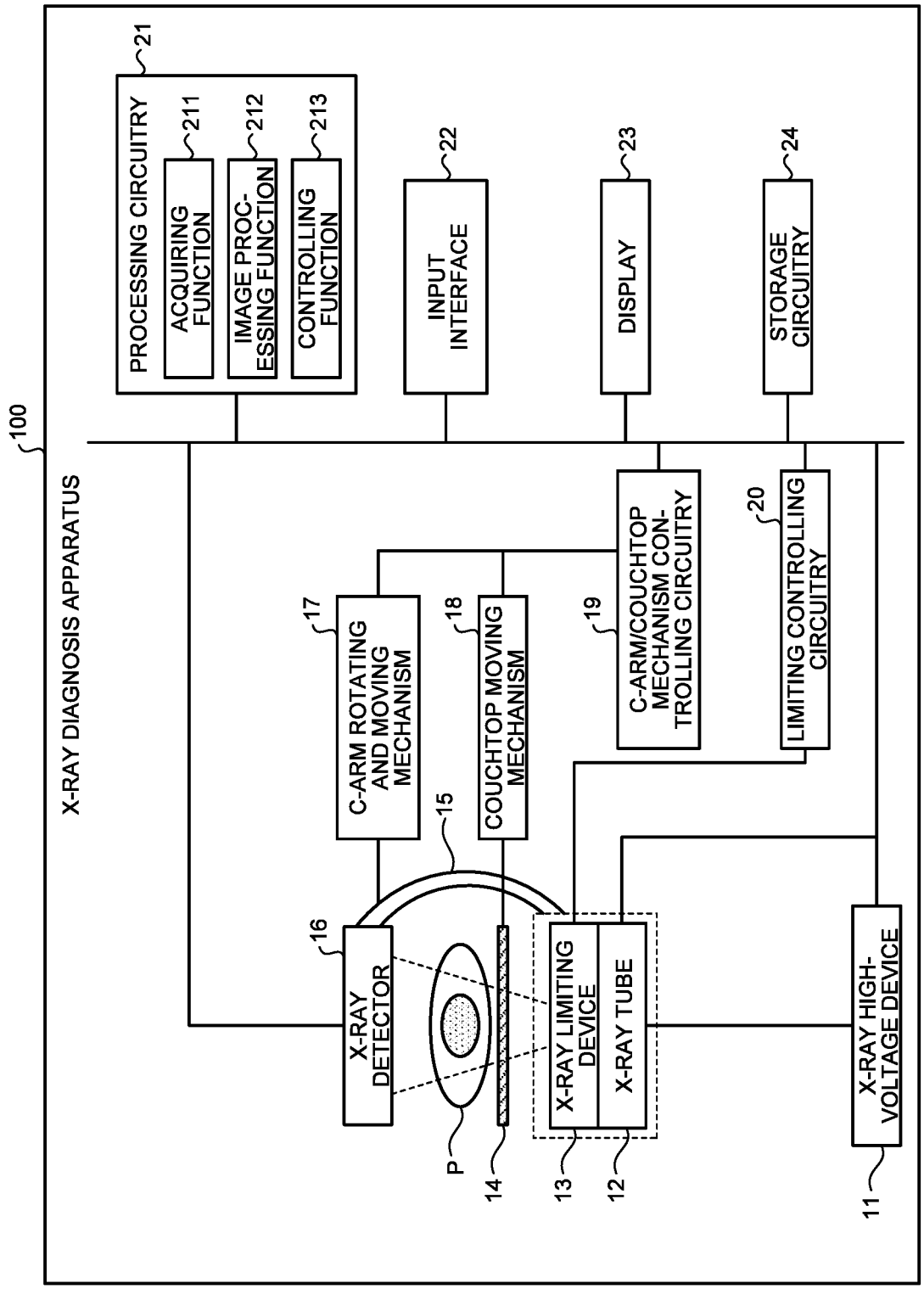
FIG. 1 is a diagram illustrating an exemplary configuration of an X-ray diagnosis apparatus according to a first embodiment.

To begin with, an overall configuration of an X-ray diagnosis apparatus according to a first embodiment will be explained. FIG. 1 is a diagram illustrating an exemplary configuration of an X-ray diagnosis apparatus 100 according to the first embodiment. As illustrated in FIG. 1, the X-ray diagnosis apparatus 100 according to the first embodiment includes an X-ray high-voltage device 11, an X-ray tube 12, an X-ray limiting device 13, a couchtop 14, a C-arm 15, an X-ray detector 16, a C-arm rotating and moving mechanism 17, a couchtop moving mechanism 18, C-arm/couchtop mechanism controlling circuitry 19, limiting controlling circuitry 20, processing circuitry 21, an input interface 22, a display 23, and storage circuitry 24.

In the X-ray diagnosis apparatus 100 illustrated in FIG. 1, processing functions are stored in the storage circuitry 24 in the form of computer-executable programs. The C-arm/couchtop mechanism controlling circuitry 19, the limiting controlling circuitry 20, and the processing circuitry 21 are processors configured to realize the functions corresponding to the programs, by reading the programs from the storage circuitry 24 and executing the read programs. In other words, the circuitries that have read the programs have the functions corresponding to the read programs.

The X-ray high-voltage device 11 is a high-voltage power source configured, under control of the processing circuitry 21, to generate high voltage and to supply the generated high voltage to the X-ray tube 12. The X-ray tube 12 is configured to generate X-rays, by using the high voltage supplied thereto from the X-ray high-voltage device 11.

The X-ray limiting device 13 is configured, under control of the limiting controlling circuitry 20, to narrow down the X-rays generated by the X-ray tube 12 so as to be selectively radiated onto a region of interest of an examined subject (hereinafter, "patient") P. For example, the X-ray limiting device 13 includes four (a plurality of) limiting blades that are slidable (movable). The limiting blades are formed by using a material such as metal that is able to restrict the radiation range of the X-rays. The limiting blades serve as an example of the X-ray blocking member.

Under the control of the limiting controlling circuitry 20, the X-ray limiting device 13 is configured to arbitrarily change the shape, the size, and the position of an opening part formed by the four limiting blades, by moving the limiting blades. As a result of the X-ray limiting device 13 adjusting the shape, the size, and the position of the opening part in this manner, the shape, the size, and the position of an X-ray radiation region on a detection surface of the X-ray detector 16 are adjusted. In other words, the X-rays generated by the X-ray tube 12 are narrowed down by the opening part of the X-ray limiting device 13 and are radiated onto the patient P. The limiting blades of the X-ray limiting device 13 are, for example, moved to positions (designated positions) designated by a user. In this situation, each of the limiting blades may be moved in a moving direction designated by the user and by a moving amount designated by the user. Further, the limiting blades may be moved so that, for example, the shape, the size, and the position of the opening part of the X-ray limiting device 13 conform to a shape, a size, and a position of the opening part designated by the user. Further, the X-ray limiting device 13 may include an additional filter used for adjusting the quality of the radiation. The additional filter is set in accordance with a medical examination to be performed, for example.

The couchtop 14 is a bed on which the patient P is placed. The couchtop 14 is arranged over a couch device (not illustrated). The patient P is not included in the X-ray diagnosis apparatus 100.

The X-ray detector 16 is configured to detect the X-rays that are emitted from the X-ray tube 12 and have passed through the patient P. For example, the X-ray detector 16 includes detecting elements arranged in a matrix formation. Each of the detecting elements is configured to convert the X-rays that have passed through the patient P into electrical signals, to accumulate the electrical signals, and to transmit the accumulated electrical signals to the processing circuitry 21. For example, the X-ray detector 16 may be realized by using a Flat Panel Detector (FPD) having the detection surface.

The C-arm 15 holds the X-ray tube 12, the X-ray limiting device 13, and the X-ray detector 16. The X-ray tube 12 with the X-ray limiting device 13 and the X-ray detector 16 are arranged by the C-arm 15 to oppose each other, while the patient P is interposed therebetween. Although FIG. 1 illustrates an example in which the X-ray diagnosis apparatus 100 is a single-plane apparatus, possible embodiments are not limited to this example. The X-ray diagnosis apparatus 100 may be a bi-plane apparatus. The C-arm 15 is caused to rotate on each of a plurality of axes individually, by an actuator such as a motor provided for a supporting device.

The C-arm rotating and moving mechanism 17 is a mechanism configured to rotate and move the C-arm 15, by driving the motor or the like provided for the supporting device, under the control of the C-arm/couchtop mechanism controlling circuitry 19. The C-arm rotating and moving mechanism 17 is also capable of changing a Source Image receptor Distance (SID), which is the distance between the X-ray tube 12 and the X-ray detector 16. The couchtop moving mechanism 18 is a mechanism configured to move the couchtop 14 under the control of the C-arm/couchtop mechanism controlling circuitry 19. For example, the couchtop moving mechanism 18 moves the couchtop 14, by using motive power generated by an actuator.

The C-arm/couchtop mechanism controlling circuitry 19 is configured to adjust the rotating and the moving of the C-arm 15 and the moving of the couchtop 14, by controlling the C-arm rotating and moving mechanism 17 and the couchtop moving mechanism 18, under the control of the processing circuitry 21. The limiting controlling circuitry 20 is configured to control the radiation range of the X-rays radiated onto the patient P, by adjusting the opening degree of the limiting blades included in the X-ray limiting device 13 so as to change the shape, the size, and the position of the opening part, under the control of the processing circuitry 21.

The input interface 22 is realized by using a joystick, a trackball, a switch button, a mouse, a keyboard, a touchpad used for performing an input operation by touching an operation surface thereof, a touch screen in which a display screen and a touchpad are integrally formed, contactless input circuitry using an optical sensor, audio input circuitry, a foot switch (a fluoroscopy-purpose foot switch) used for causing X-ray radiation in fluoroscopy processes, and/or the like.

The input interface 22 is connected to the processing circuitry 21 and is configured to convert an input operation received from the user into an electrical signal, and to output the electrical signal to the processing circuitry 21. The input interface 22 does not necessarily have to include one or more physical operation component parts such as a joystick, a mouse, and a keyboard. For example, possible examples of the input interface include processing circuitry configured to receive an electrical signal corresponding to an input operation from an external input device provided separately from the X-ray diagnosis apparatus 100 and to output the electrical signal to the processing circuitry 21. The input interface 22 is an example of an input unit.

The display 23 is configured to display a Graphical User Interface (GUI) used for receiving instructions from the user and images represented by various types of images generated by the processing circuitry 21. Further, the display 23 is configured to display various types of processing results and analysis results obtained by the processing circuitry 21. The display 23 is an example of a display unit.

The storage circuitry 24 is configured to receive various types of image data generated by the processing circuitry 21 and to store therein the received image data.

Further, the storage circuitry 24 has stored therein computer programs (hereinafter, "programs") that correspond to the various types of functions and are read and executed by the circuitries illustrated in FIG. 1. In one example, the storage circuitry 24 stores therein a program corresponding to an acquiring function 211, a program corresponding to an image processing function 212, and a program corresponding to a controlling function 213 that are read and executed by the processing circuitry 21. With reference to FIG. 1, the example was explained in which the single storage circuitry (i.e., the storage circuitry 24) stores therein the programs corresponding to the processing functions; however, another arrangement is also acceptable in which a plurality of storage circuitries are provided in a distributed manner so that various types of circuitries including the processing circuitry 21 each read a corresponding one of the programs from one of the individual storage circuitries. The storage circuitry 24 is an example of a storage unit.

The processing circuitry 21 is configured to control operations of the entirety of the X-ray diagnosis apparatus 100 by executing the acquiring function 211, the image processing function 212, and the controlling function 213. More specifically, by reading and executing the program corresponding to the acquiring function 211 from the storage circuitry 24, the processing circuitry 21 is configured to perform various types of processes related to acquiring the X-ray image data. For example, the acquiring function 211 is configured to generate the X-ray image data by using the electrical signals converted from the X-rays by the X-ray detector 16 and to store the generated X-ray image data into the storage circuitry 24. In one example, the acquiring function 211 generates projection data based on the electrical signals, by performing a current/voltage conversion, an Analog-to-Digital (A/D) conversion, and/or a parallel/serial conversion on the electrical signals received from the X-ray detector 16. Further, the acquiring function 211 stores the generated projection data into the storage circuitry 24. Further, the acquiring function 211 is also capable of reconstructing reconstruction data (volume data) by using projection data acquired through a rotating imaging process and further storing the reconstructed volume data into the storage circuitry 24.

Further, by reading and executing the program corresponding to the image processing function 212 from the storage circuitry 24, the processing circuitry 21 is configured to execute various types of processes related to image processing processes. For example, the image processing function 212 is configured to control image processing processes and analyzing processes performed on the projection data. In one example, the image processing function 212 generates X-ray image data by performing various types of image processing processes on the projection data stored in the storage circuitry 24. Alternatively, the image processing function 212 may generate X-ray image data by obtaining projection data directly from the acquiring function 211 and performing various types of image processing processes on the obtained projection data.

In this situation, the image processing function 212 stores the X-ray image data resulting from the image processing processes into the storage circuitry 24. For example, the image processing function 212 is capable of performing various types of processes using an image processing filter such as a moving average (smoothing) filter, a Gaussian filter, a median filter, a recursive filter, a band-pass filter, or the like. Further, the image processing function 212 is also capable of generating a three-dimensional image from the volume data.

Further, by reading and executing the program corresponding to the controlling function 213 that controls the entirety of the X-ray diagnosis apparatus 100 from the storage circuitry 24, the processing circuitry 21 is configured to perform various types of processes related to the overall control. For example, the controlling function 213 is configured to control the amount of X-rays to be radiated onto the patient P and turning on and off the X-rays, by controlling the X-ray high-voltage device 11 so as to adjust the voltage supplied to the X-ray tube 12, according to an instruction from the user transferred thereto from the input interface 22. Further, for example, the controlling function 213 is configured to adjust the rotating and the moving of the C-arm 15 and the moving of the couchtop 14, by controlling the C-arm/couchtop mechanism controlling circuitry 19 according to an instruction from the user.

Further, for example, the controlling function 213 is configured to control the radiation range of the X-rays radiated onto the patient P, by controlling the limiting controlling circuitry 20 and adjusting the opening degree of the limiting blades included in the X-ray limiting device 13, according to an instruction from the user received by the input interface. Further, the controlling function 213 is configured to control the display 23 so as to display a GUI used for receiving instructions from the user, as well as images represented by any of the image data stored in the storage circuitry 24, processing results obtained by the processing circuitry 21, and the like. The controlling function 213 serves as examples of a controlling unit and a display controlling unit.

Figure 2:
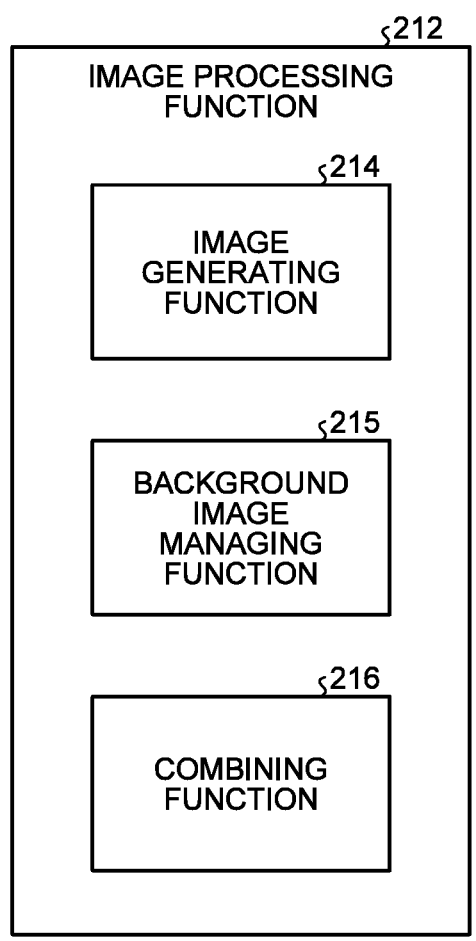
FIG. 2 is a diagram illustrating an exemplary configuration of an image processing function according to the first embodiment.

FIG. 2 is a diagram illustrating an exemplary configuration of the image processing function 212 according to the first embodiment. As illustrated in FIG. 2, the image processing function 212 includes an image generating function 214, a background image managing function 215, and a combining function 216. The image generating function 214 is an example of a first generating unit. The background image managing function 215 is an example of a managing unit. The combining function 216 is an example of a specifying unit and is an example of a second generating unit. Processes performed by the image generating function 214, the background image managing function 215, and the combining function 216 will be explained in detail later.

An overall configuration of the X-ray diagnosis apparatus 100 has thus been explained. When partial fluoroscopy is implemented, for example, it is possible that the user may set a region of interest. In that situation, because the user needs to set the region of interest in advance, the operation can become cumbersome. To cope with this situation, the X-ray diagnosis apparatus 100 according to the present embodiment performs various types of processes described below, so that it is possible to improve operability in the implementation of the partial fluoroscopy. For example, the X-ray diagnosis apparatus 100 improves the operability in the implementation of the partial fluoroscopy, by having the partial fluoroscopy executed without requiring the user to set a region of interest.

Figure 3:
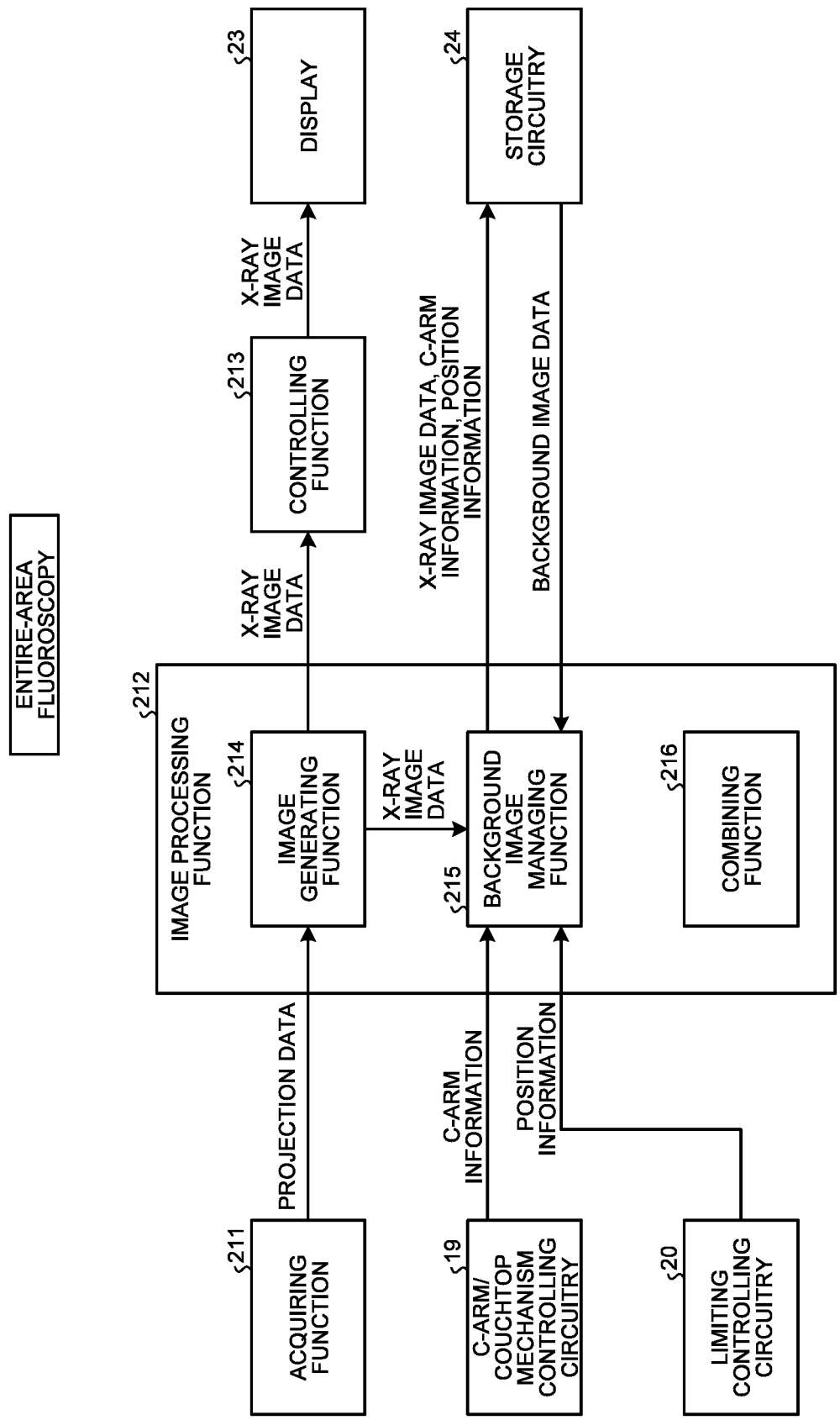
FIG. 3 is a chart for explaining an example of processes performed by the X-ray diagnosis apparatus according to the first embodiment.

An example will be explained in which the user causes partial fluoroscopy to be executed, while the X-ray diagnosis apparatus 100 is performing a normal fluoroscopy process (entire-area fluoroscopy). FIG. 3 is a chart for explaining an example of processes performed by the X-ray diagnosis apparatus 100 according to the first embodiment. FIG. 3 illustrates the example of the processes performed by the X-ray diagnosis apparatus 100 when implementing the entire-area fluoroscopy.

When the user presses the fluoroscopy-purpose foot switch during a manipulation of intervention treatment, the acquiring function 211 acquires projection data obtained by taking an image of the patient P under a fluoroscopy image taking condition and, as illustrated in FIG. 3, transmits the acquired projection data to the image generating function 214. In this situation, the opening part of the X-ray limiting device 13 is fully open, so that the opening degree of the opening part is at a maximum. In other words, the acquiring function 211 acquires the acquisition data obtained by performing the image taking process while the opening part of the X-ray limiting device 13 is fully open. In this situation, while the fluoroscopy-purpose foot switch is pressed, the acquiring function 211 sequentially transmits the projection data to the image processing function 212, frame by frame. While the fluoroscopy-purpose foot switch is not pressed, because the acquiring function 211 stops the acquisition of the projection data, no projection data is transmitted to the image processing function 212. In other words, only while the fluoroscopy-purpose foot switch is pressed, the entire-area fluoroscopy and the partial fluoroscopy are performed.

Every time one frame of projection data is received, the image generating function 214 generates one frame of X-ray image data (real-time image data, fluoroscopic image data) by performing various types of image processing processes on the received projection data. After that, every time one frame of X-ray image data is generated, the image processing function 212 transmits the one frame of X-ray image data having been generated, to the controlling function 213 and the background image managing function 215.

Figure 4:
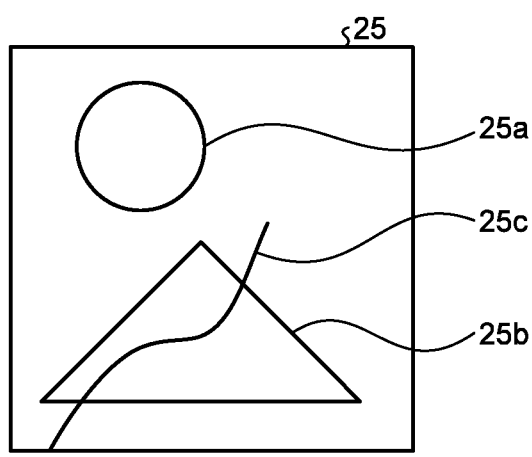
FIG. 4 is a drawing illustrating a schematic example of a fluoroscopic image obtained by entire-area fluoroscopy according to the first embodiment.

Every time one frame of X-ray image data is received, the controlling function 213 causes the display 23 to display an X-ray image (a fluoroscopic image) represented by the received X-ray image data. In other words, the controlling function 213 causes the display 23 to sequentially display X-ray images. Accordingly, the display 23 sequentially displays fluoroscopic images obtained by the entire-area fluoroscopy. In other words, the display 23 is configured to display the fluoroscopic images obtained by the entire-area fluoroscopy in a real-time manner. FIG. 4 is a drawing illustrating a schematic example of a fluoroscopic image obtained by the entire-area fluoroscopy according to the first embodiment. For example, the display 23 sequentially displays a fluoroscopic image 25 illustrated in FIG. 4 obtained by the entire-area fluoroscopy. The fluoroscopic image 25 renders sites 25a and 25b of the patient P and a medical device 25c such as a catheter used in the intervention treatment.

Further, the C-arm/couchtop mechanism controlling circuitry 19 transmits information (C-arm information) including the clinical angle and the SID of the C-arm 15 to the background image managing function 215. For example, the C-arm/couchtop mechanism controlling circuitry 19 transmits the most recent C-arm information in synchronization with the timing with which the image generating function 214 transmits the X-ray image data to the background image managing function 215. As a result, the background image managing function 215 receives the X-ray image data substantially at the same time as the receiving of the C-arm information corresponding to the time of the generation of the X-ray image data. Accordingly, the background image managing function 215 is able to keep the X-ray image data in correspondence with the C-arm information corresponding to the X-ray image data. Alternatively, the C-arm/couchtop mechanism controlling circuitry 19 may transmit the most recent C-arm information while being out of synchronization with the timing with which the image generating function 214 transmits the X-ray image data to the background image managing function 215. In that situation, the background image managing function 215 brings the received most recent C-arm information into correspondence with the most recent X-ray image data that has already been received at the time of the reception of the most recent C-arm information. As a result, the X-ray image data is kept in correspondence with the C-arm information corresponding to the X-ray image data.

Further, from the X-ray limiting device 13, the limiting controlling circuitry 20 obtains position information indicating the positions of the four limiting blades included in the X-ray limiting device 13 and further transmits the obtained position information to the background image managing function 215. For example, the limiting controlling circuitry 20 transmits the most recent position information in synchronization with the timing with which the image generating function 214 transmits the X-ray image data to the background image managing function 215. As a result, the background image managing function 215 receives the X-ray image data substantially at the same time as the receiving of the position information corresponding to the time of the generation of the X-ray image data. Accordingly, the background image managing function 215 is able to keep the X-ray image data in correspondence with the position information corresponding to the X-ray image data. Alternatively, the limiting controlling circuitry 20 may transmit the most recent position information while being out of synchronization with the timing with which the image generating function 214 transmits the X-ray image data to the background image managing function 215. In that situation, the background image managing function 215 brings the received most recent position information into correspondence with the most recent X-ray image data that has already been received at the time of the reception of the most recent position information. As a result, the X-ray image data is kept in correspondence with the position information corresponding to the X-ray image data.

Further, the background image managing function 215 stores the X-ray image data, the C-arm information, and the position information into the storage circuitry 24 so as to be kept in correspondence with one another.

Next, an example will be explained in which the user views the fluoroscopic image 25 obtained by the entire-area fluoroscopy and subsequently switches from the entire-area fluoroscopy to the partial fluoroscopy for the purpose of checking the image by narrowing down the range. In that situation, the X-ray diagnosis apparatus 100 according to the present embodiment is configured to switch from the entire-area fluoroscopy to the partial fluoroscopy, as described below, by prompting the user to narrow the opening part of the X-ray limiting device 13, without requiring the user to set a region of interest.

When switching from the entire-area fluoroscopy to the partial fluoroscopy, the user operates the input interface 22 and inputs an instruction to designate positions of the limiting blades, to narrow the opening part of the X-ray limiting device 13. On the basis of the input instruction, the limiting controlling circuitry 20 moves the limiting blades to the positions designated by the user. In this situation, to narrow the opening part of the X-ray limiting device 13, it is sufficient when the user inputs an instruction to designate the position of at least one of the four limiting blades. In that situation, on the basis of the input instruction, the limiting controlling circuitry 20 moves the limiting blade designated to be moved, to the position designated by the user.

Alternatively, the user may operate the input interface 22 and input an instruction to move an opposing pair of limiting blades among the four limiting blades, to narrow the opening part of the X-ray limiting device 13.

Further, the user may operate the input interface 22 and input an instruction to designate a moving direction and a moving amount of at least one of the four limiting blades, to narrow the opening part of the X-ray limiting device 13. In that situation, on the basis of the input instruction, the limiting controlling circuitry 20 moves the limiting blade designated to be moved, in the moving direction designated by the user and by the moving amount designated by the user. For example, the user may designate the moving direction and the moving amount of the limiting blade, by operating four operating units (e.g., a joystick) provided in the input interface 22 and corresponding to the four limiting blades of the X-ray limiting device. In that situation, the direction of the operation performed on the operating unit corresponds to the moving direction of the corresponding limiting blade. Further, the time period during which the operation is continually performed on the operating unit corresponds to the moving amount of the corresponding limiting blade. Further, the user may operate the input interface 22 and input an instruction to designate a shape, a size, and a position of the opening part, to narrow the opening part of the X-ray limiting device 13. In that situation, on the basis of the input instruction, the limiting controlling circuitry 20 moves at least one of the four limiting blades of the X-ray limiting device 13, so that the shape, the size, and the position of the opening part conform to the shape, the size, and the position designated by the user.

In this situation, the background image managing function 215 is monitoring at all times the positions of the four limiting blades indicated in the position information sequentially transmitted thereto from the limiting controlling circuitry 20. For example, the background image managing function 215 compares the positions of the four limiting blades indicated in a piece of position information with the positions of the four limiting blades indicated in another piece of position information received immediately prior to the piece of position information, and judges whether or not a change occurred in the positions of the limiting blades every time one piece of position information is received. For example, the background image managing function 215 judges whether or not the opening part of the X-ray limiting device 13 has been narrowed.

When the background image managing function 215 determines that no change occurred in the positions of the limiting blades, the fluoroscopy process that has so far been performed is continued. On the contrary, when having determined that a change occurred in the positions of the limiting blades (e.g., when having determined that the opening part has been narrowed), the background image managing function 215 refers to what is stored in the storage circuitry 24 and obtains X-ray image data used as background image data representing a background image in the partial fluoroscopy.

In a specific example, the background image managing function 215 refers to what is stored in the storage circuitry 24 and specifies a plurality of pieces of X-ray image data and position information kept in correspondence with C-arm information that matches the most recent C-arm information (i.e., the C-arm information at the time of determining that a change occurred in the positions of the limiting blades). In this situation, the clinical angle and the SID indicated in the C-arm information are geometrical conditions related to the image taking process. In this situation, with respect to all of the specified pieces of position information, the background image managing function 215 calculates the opening degree of the opening part of the X-ray limiting device 13 on the basis of the position information. Further, the background image managing function 215 obtains, as the background image data, such a piece of X-ray image data that is kept in correspondence with the position information corresponding to the largest opening degree of the opening part of the X-ray limiting device 13 among the specified plurality of pieces of X-ray image data. In other words, with respect to a clinical angle and an SID that are equal to the clinical angle and the SID corresponding to the time of the generation of the X-ray image data by the image generating function 214, the background image managing function 215 obtains, as the background image data, such a piece of X-ray image data corresponding to the largest opening degree of the opening part formed by the limiting blades, among the plurality of pieces of X-ray image data generated by the image generating function 214.

In this situation, when there are two or more pieces of X-ray image data that are kept in correspondence with the position information corresponding to the largest opening degree of the opening part, the background image managing function 215 obtains the most recent piece of X-ray image data among the two or more pieces of X-ray image, data as the background image data. Further, the background image managing function 215 saves the background image data. For example, the background image managing function 215 saves the background image data by storing the background image data into the storage circuitry 24.

After that, when the background image managing function 215 has obtained the background image data, the controlling function 213 included in the X-ray diagnosis apparatus 100 switches from the entire-area fluoroscopy to the partial fluoroscopy. In other words, as being triggered by the change made by the user to the positions of the limiting blades of the X-ray limiting device 13, the controlling function 213 controls the entirety of the X-ray diagnosis apparatus 100 so as to start the partial fluoroscopy.

Figure 5:
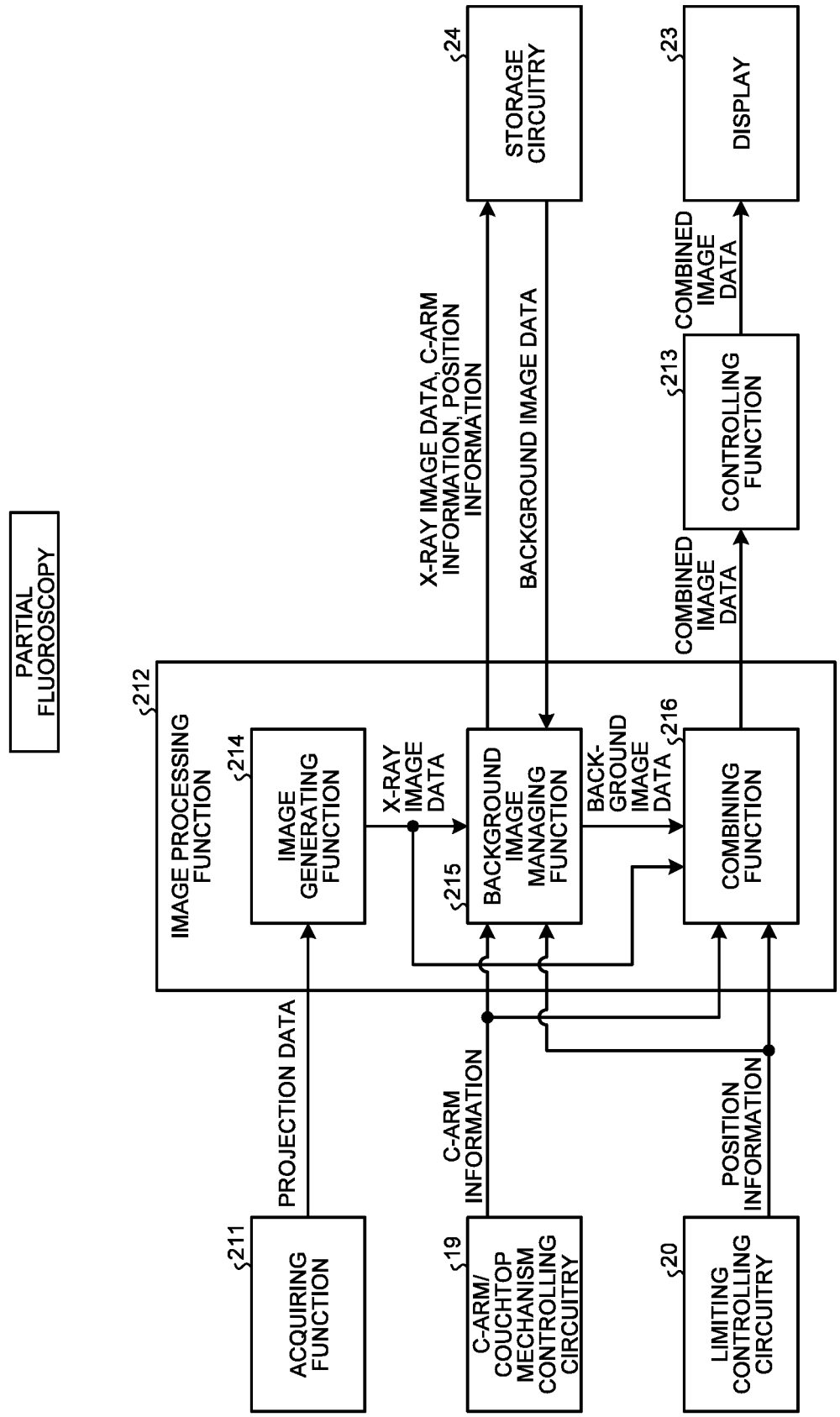
FIG. 5 is a chart for explaining an example of processes performed by the X-ray diagnosis apparatus according to the first embodiment.

FIG. 5 is a chart for explaining an example of processes performed by the X-ray diagnosis apparatus 100 according to the first embodiment. FIG. 5 illustrates the example of the processes performed by the X-ray diagnosis apparatus 100 when implementing the partial fluoroscopy. In the partial fluoroscopy also, the acquiring function 211 acquires projection data and sequentially transmits, as illustrated in FIG. 5, the acquired projection data to the image processing function 212 frame by frame, similarly to the example of the entire-area fluoroscopy.

In this situation, immediately after the partial fluoroscopy is started, the limiting blades are in the process of moving from the positions corresponding to being fully open (fully-open positions) toward the positions designated by the user (the designated positions). Further, the limiting blades subsequently become stationary in the designated positions. For this reason, the pieces of projection data transmitted by the acquiring function 211 to the image processing function 212 in the partial fluoroscopy include pieces of projection data acquired while the limiting blades are moving from the fully-open positions to the designated positions and pieces of projection data acquired while the limiting blades are stationary in the designated positions.

In the partial fluoroscopy also, every time one frame of projection data is received, the image generating function 214 generates one frame of X-ray image data by performing the various types of image processing process on the received projection data, similarly to the example of the entire-area fluoroscopy. Further, every time one frame of X-ray image data is generated, the image processing function 212 transmits the one frame of X-ray image data having been generated, to the background image managing function 215 and the combining function 216.

Further, in the partial fluoroscopy also, the C-arm/couch-top mechanism controlling circuitry 19 transmits C-arm information to the background image managing function 215, similarly to the example of the entire-area fluoroscopy. Further, in the partial fluoroscopy, the C-arm/couchtop mechanism controlling circuitry 19 transmits the C-arm information also to the combining function 216.

Further, in the partial fluoroscopy also, the limiting controlling circuitry 20 obtains position information indicating the positions of the four limiting blades of the X-ray limiting device 13 from the X-ray limiting device 13 and further transmits the obtained position information to the background image managing function 215, similarly to the example of the entire-area fluoroscopy. Further, in the partial fluoroscopy, the limiting controlling circuitry 20 transmits the position information also to the combining function 216.

In this situation, the C-arm/couchtop mechanism controlling circuitry 19 and the limiting controlling circuitry 20 transmit the C-arm information and the position information to the combining function 216, substantially at the same time as the transmitting of the C-arm information and the position information to the background image managing function 215. Accordingly, similarly to the background image managing function 215 described above, the combining function 216 is able to keep the X-ray image data in correspondence with the C-arm information and the position information corresponding to the X-ray image data.

Further, in the partial fluoroscopy also, the background image managing function 215 stores the X-ray image data, the C-arm information, and the position information into the storage circuitry 24 so as to be kept in correspondence with one another, similarly to the example of the entire-area fluoroscopy. Further, in the partial fluoroscopy, the background image managing function 215 transmits the obtained background image data to the combining function 216.

Every time one frame of X-ray image data is received, the combining function 216 generates one frame of combined image data (partial fluoroscopic image data), by combining the most recent background image data with the received X-ray image data, while using the C-arm information and the position information corresponding to the X-ray image data. The received X-ray image data is an example of the first X-ray image data. Further, the background image data is an example of the second X-ray image data. The combined image data according to the first embodiment is an example of the first combined image data.

Figure 6:
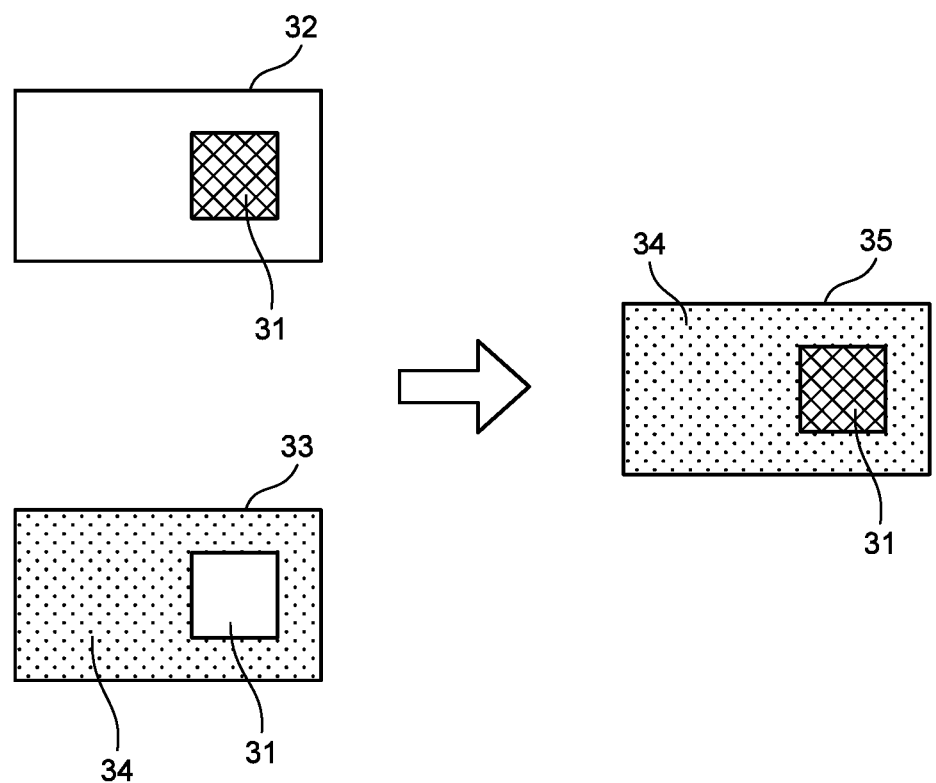
FIG. 6 is a drawing for explaining an example of a method for generating combined image data according to the first embodiment.

FIG. 6 is a drawing for explaining an example of a method for generating the combined image data according to the first embodiment. As illustrated in FIG. 6, for example, the combining function 216 specifies a radiation region 31 within X-ray image data 32 to be combined with background image data 33. The radiation region 31 is a region of an image generated on the basis of electrical signals from the detecting elements radiated with the X-rays emitted from the X-ray tube 12, among the plurality of detecting elements arranged in the matrix formation in the X-ray detector 16.

For example, on the basis of the position information and the C-arm information, the combining function 216 specifies the X-ray radiation range (the radiation region) on the detection surface of the X-ray detector 16. In this regard, possible situations of the position information include both of the following: the position information indicates the positions of the limiting blades during the move; and the position information indicates the positions of the limiting blades after the move. Further, the combining function 216 specifies the radiation region 31 that is the region within the X-ray image data 32 corresponding to the specified X-ray radiation region on the detection surface. In other words, on the basis of the position information indicating the positions of the limiting blades during the move and after the move, the combining function 216 specifies the radiation region 31 of the X-rays within each piece of X-ray image data 32 generated by the image generating function 214.

After that, as illustrated in FIG. 6, the combining function 216 generates combined image data 35 by using the specified radiation region 31. For example, the combining function 216 generates the combined image data 35, by using the pixel values of the pixels in the radiation region 31 within the X-ray image data 32 as the pixel values of the pixels in the radiation region 31 among the plurality of pixels structuring the combined image data 35 and also using the pixel values of the pixels in a region 34 other than the radiation region 31 within the most recent background image data 33 as the pixel values of the pixels in the region 34 among the plurality of pixels structuring the combined image data 35.

In this manner, the combining function 216 generates the combined image data 35 by combining the X-ray image data 32 related to the region of interest defined by the limiting blades that individually move on the basis of the operation received by the input interface 22, with the background image data 33 generated prior to the move of the limiting blades.

Further, the combining function 216 may generate the combined image data 35 by using image data representing a line that has a predetermined width or image data in which the pixel values are inverted, as the image data in a part corresponding to the boundary between the radiation region 31 and the region 34.

Further, every time one frame of combined image data is generated, the combining function 216 transmits the one frame of combined image data having been generated, to the controlling function 213.

Every time one frame of combined image data is received, the controlling function 213 causes the display 23 to display a combined image (a partial fluoroscopic image) represented by the received combined image data (the partial fluoroscopic image data). Accordingly, the display 23 sequentially displays partial fluoroscopic images obtained by the partial fluoroscopy. In other words, the display 23 is configured to display the partial fluoroscopic images in a real-time manner.

Figure 7A:
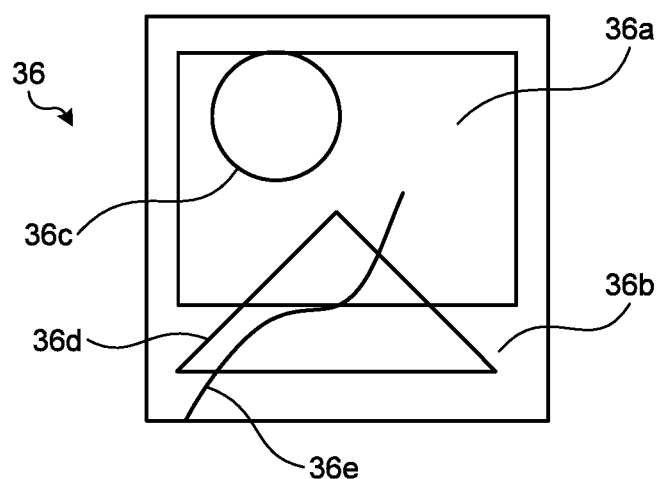
FIG. 7A is a drawing illustrating a schematic example of a partial fluoroscopic image obtained by partial fluoroscopy according to the first embodiment.
Figure 7B:
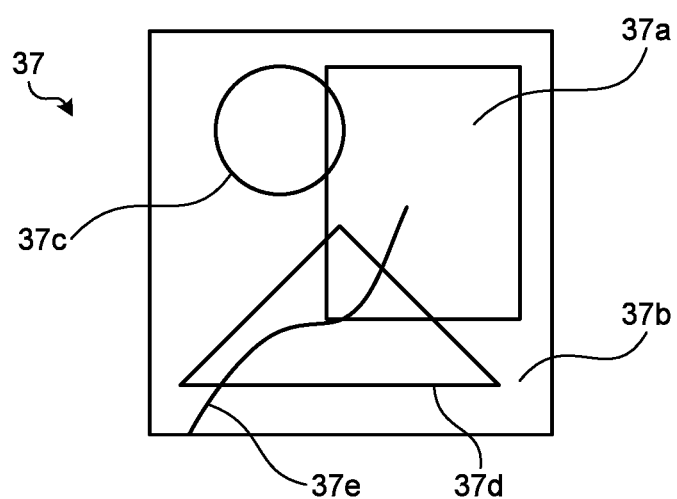
FIG. 7B is a drawing illustrating another schematic example of a partial fluoroscopic image obtained by the partial fluoroscopy according to the first embodiment.

FIGS. 7A and 7B are drawings illustrating schematic examples of partial fluoroscopic images obtained by the partial fluoroscopy according to the first embodiment. FIG. 7A illustrates a combined image 36 represented by combined image data generated on the basis of projection data acquired while the limiting blades are moving from the fully-open positions to the designated positions, immediately after the partial fluoroscopy is started. Further, FIG. 7B illustrates a combined image 37 represented by combined image data generated on the basis of projection data acquired when the limiting blades have become stationary in the designated positions.

The combined image 36 is an image in which a real-time image 36a represented by the X-ray image generated on the basis of the projection data acquired during the move of the limiting blades is superimposed on a background image 36b represented by the background image data generated on the basis of the projection data acquired prior to the move of the limiting blades. The combined image 36 renders sites 36c and 36d of the patient P and a medical device 36e.

The combined image 37 is an image in which a real-time image 37a represented by the X-ray image data generated on the basis of the projection data acquired after the move of the limiting blades is superimposed on a background image 37b represented by the background image data generated on the basis of the projection data acquired prior to the move of the limiting blades. The combined image 37 renders sites 37c and 37d of the patient P and a medical device 37e.

In this situation, the background image 36b and the background image 37b are the same image as each other. The site 36c and the site 37c are the same site as each other, while the site 36d and the site 37d are the same site as each other. Further, the medical device 36e and the medical device 37e are the same medical device as each other.

In the transition from FIG. 7A to 7B, as the size of the real-time image (the real-time images 36a and 37a) gradually decreases, the size of the background image (the background images 36b and 37b) gradually increases. In other words, the X-ray diagnosis apparatus 100 according to the present embodiment generates the partial fluoroscopic image data so that the background image is displayed in a non-X-ray-radiation part of the partial fluoroscopic image, in conjunction with the narrowing process performed by the user on the limiting blades of the X-ray limiting device 13.

Accordingly, by using the X-ray diagnosis apparatus 100 according to the present embodiment, it is possible to implement the partial fluoroscopy only with the simple operation of narrowing the opening part of the X-ray limiting device 13 simply performed by the user to narrow down the range he/she wishes to check, without requiring the user to set a region of interest. Further, by using the X-ray diagnosis apparatus 100, it is possible to implement the partial fluoroscopy, without making the user conscious of the implementation of the partial fluoroscopy by having the user set a region of interest. Further, by using the X-ray diagnosis apparatus 100, it is possible to implement the two types of fluoroscopy, namely the entire-area fluoroscopy and the partial fluoroscopy, only by using the one type of fluoroscopy-purpose foot switch. Consequently, by using the X-ray diagnosis apparatus 100 according to the first embodiment, it is possible to improve operability in the implementation of the partial fluoroscopy. As a result, it is expected that throughput of medical examinations will be enhanced and that the radiation exposure will be reduced.

An example was explained above in which the X-ray diagnosis apparatus 100 switches from the entire-area fluoroscopy to the partial fluoroscopy, as being triggered, during the implementation of the entire-area fluoroscopy, when it is determined that the user made a change to the positions of the limiting blades of the X-ray limiting device 13. In contrast, when it is determined that a change is made to the positions of the limiting blades of the X-ray limiting device 13 during the implementation of the partial fluoroscopy, the X-ray diagnosis apparatus 100 according to the first embodiment continues the implementation of the partial fluoroscopy by using newly-obtained background image data. For example, when it is determined that a change is made to the positions of the limiting blades during the implementation of the partial fluoroscopy, the X-ray diagnosis apparatus 100 discards the background image data that has so far been saved, obtains a new piece of background image data by using the same method as the background image data obtaining method described above, and saves the new obtained piece of background image data. Consequently, by using the X-ray diagnosis apparatus 100 according to the present embodiment, it is possible to continue the implementation of the partial fluoroscopy, without requiring the user to newly set a region of interest. Consequently, in this aspect also, it is possible to improve operability in the implementation of the partial fluoroscopy, by using the X-ray diagnosis apparatus 100 according to the first embodiment.

Further, when a change occurred in the C-arm information during the implementation of the partial fluoroscopy, the background image managing function 215 discards the background image data, whereas the controlling function 213 controls the entirety of the X-ray diagnosis apparatus 100 so that the entire-area fluoroscopy is implemented. For example, every time a piece of C-arm information is received, the background image managing function 215 compares the received piece of C-arm information with another piece of C-arm information received immediately prior to the piece of C-arm information and judges whether or not a change occurred in the C-arm information. Further, when it is determined that a change occurred in the C-arm information, the background image managing function 215 discards the background image data by deleting the background image data stored in the storage circuitry 24.

Next, an example of a flow in the processes performed by the X-ray Diagnosis apparatus 100 will be explained, with reference to FIG. 8. FIG. 8 is a flowchart for explaining an example of the flow in the processes performed by the X-ray diagnosis apparatus 100 according to the first embodiment. These processes are performed when the fluoroscopy-purpose foot switch is pressed. Further, these processes are ended when the fluoroscopy-purpose foot switch is released.

As illustrated in FIG. 8, the X-ray diagnosis apparatus 100 starts implementing the entire-area fluoroscopy (step S101). Further, the X-ray diagnosis apparatus 100 judges whether or not a change occurred in the positions of the limiting blades (step S102). When the X-ray diagnosis apparatus 100 determines that no change occurred in the positions of the limiting blades (step S102: No), the process returns to step S101 where the implementation of entire-area fluoroscopy is continued so that the judging process at step S102 is performed again.

On the contrary, when having determined that a change occurred in the positions of the limiting blades (step S102: Yes), the X-ray diagnosis apparatus 100 obtains background image data (step S103). After that, the X-ray diagnosis apparatus 100 switches from the entire-area fluoroscopy to the partial fluoroscopy and starts implementing the partial fluoroscopy by using the obtained background image data (step S104).

Subsequently, the X-ray diagnosis apparatus 100 judges whether or not a change occurred in the positions of the limiting blades in the partial fluoroscopy (step S105). When having determined that a change occurred in the positions of the limiting blades in the partial fluoroscopy (step S105: Yes), the X-ray diagnosis apparatus 100 newly obtains background image data (step S106). After that, the X-ray diagnosis apparatus 100 returns to step S104 where the X-ray diagnosis apparatus 100 implements the partial fluoroscopy by using the newly-obtained background image data, so that the judging process at step S105 is performed again.

On the contrary, when having determined that no change occurred in the positions of the limiting blades in the partial fluoroscopy (step S105: No), the X-ray diagnosis apparatus 100 judges whether or not a change occurred in the C-arm information during the implementation of the partial fluoroscopy (step S107). When having determined that no change occurred in the C-arm information during the implementation of the partial fluoroscopy (step S107: No), the X-ray diagnosis apparatus 100 returns to step S104 where the X-ray diagnosis apparatus 100 continues the partial fluoroscopy, so that the judging process at step S105 is performed again.

On the contrary, when having determined that a change occurred in the C-arm information during the implementation of the partial fluoroscopy (step S107: Yes), the X-ray diagnosis apparatus 100 discards the background image data (step S108) and returns to step S101 where the X-ray diagnosis apparatus 100 switches from the partial fluoroscopy to the entire-area fluoroscopy and starts implementing the entire-area fluoroscopy.

The first embodiment has thus been explained. As explained above, in the first embodiment, the X-ray tube 12 is configured to generate the X-rays. The X-ray detector 16 is configured to detect the X-rays emitted from the X-ray tube 12. The image generating function 214 is configured to sequentially generate the X-ray image data based on the detection result obtained by the X-ray detector 16. The storage circuitry 24 is configured to store therein the X-ray image data generated by the image generating function 214. The X-ray limiting device 13 includes the movable limiting blades and is configured to restrict the range radiated with the X-rays emitted from the X-ray tube 12. The input interface 22 is configured to receive the operation to move the limiting blades. Examples of the operation include an operation to move at least one of the plurality of limiting blades; and an operation to move an opposing pair of limiting blades among the four limiting blades. The combining function 216 is configured to specify the radiation region of the X-rays in the pieces of X-ray image data generated by the image generating function 214, during the move of the limiting blades that are moved by the X-ray limiting device 13 on the basis of the operation received by the input interface 22. Further, by using the specified radiation region, the combining function 216 is configured to sequentially generate, during the move of the limiting blades, the combined image data, by combining the X-ray image data generated by the image generating function 214 during the move of the limiting blades, with the background image data generated by the image generating function 214 prior to the move of the limiting blades and stored in the storage circuitry 24. The controlling function 213 is configured to cause the display 23 to display the combined image represented by the combined image data. As explained above, by using the X-ray diagnosis apparatus 100 according to the first embodiment, it is possible to improve operability in the implementation of the partial fluoroscopy.

In the first embodiment, when an instruction is received from the user via the input interface 22 indicating that the real-time image in the combined image displayed on the display 23 should be enlarged or reduced by a predetermined ratio, for example, the image generating function 214 may perform the following process: For instance, by using the real-time image data, the image generating function 214 may generate enlarged real-time image data enlarged by the predetermined ratio or may generate reduced real-time image data reduced by the predetermined ratio. Further, the controlling function 213 may cause the display 23 to display an enlarged real-time image represented by the enlarged real-time image data or may cause the display 23 to display a reduced real-time image represented by the reduced real-time image data.

Further, in conjunction with the enlargement or the reduction of the real-time image, the image generating function 214 may, by using the background image data, similarly generate enlarged background image data enlarged by the predetermined ratio or similarly generate reduced background image data reduced by the predetermined ratio. Further, the controlling function 213 may cause the display 23 to display an enlarged background image represented by the enlarged background image data or may cause the display 23 to display a reduced background image represented by the reduced background image data.

First Modification Example of First Embodiment

In the first embodiment above, the example was explained in which, when a change occurred in the C-arm information during the implementation of the partial fluoroscopy, the X-ray diagnosis apparatus 100 discards the background image data and switches from the partial fluoroscopy to the entire-area fluoroscopy, so that the entire-area fluoroscopy is implemented; however, even when a change occurred during the implementation of the partial fluoroscopy, the X-ray diagnosis apparatus 100 may continue the partial fluoroscopy. Thus, this embodiment will be explained as a first modification example of the first embodiment. Some of the configurations that are the same as those in the first embodiment will be referred to by using the same reference characters, and the explanations thereof may be omitted.

FIG. 9 is a chart for explaining an example of processes performed by the X-ray diagnosis apparatus 100 according to the first modification example of the first embodiment. FIG. 9 illustrates the example of the processes performed by the X-ray diagnosis apparatus 100 according to the first modification example when implementing the partial fluoroscopy. Because the entire-area fluoroscopy according to the first embodiment is the same process as the entire-area fluoroscopy according to the first modification example, the explanation of the entire-area fluoroscopy according to the first modification example will be omitted. Further, in the description of the first modification example below, a focus will be placed on differences from the partial fluoroscopy according to the first embodiment, and the explanations of certain configurations that are the same will be omitted.

When a change occurred in the C-arm information during the implementation of the partial fluoroscopy, the X-ray diagnosis apparatus 100 according to the first modification example continues the partial fluoroscopy without discarding the background image data, as described below.

For example, when it is determined that a change occurred in the C-arm information, the background image managing function 215 transmits a fully-open/restore instruction to the limiting controlling circuitry 20. In this situation, the fully-open/restore instruction instructs that, for example, the positions of the limiting blades should be moved from the positions (restoration positions) of the limiting blades at the time of the determination that the change occurred in the C-arm information, to the positions with an opening degree at a maximum (a maximum opening degree) where the opening part of the X-ray limiting device 13 is fully open, and subsequently, that the positions of the limiting blades should be moved so that the positions of the limiting blades return to the restoration positions. In this situation, the restoration positions are, for example, when a change occurred in the clinical angle and the SID indicated in the C-arm information, the positions corresponding to the opening degree of the opening part of the X-ray limiting device 13 observed at the time of the change in the clinical angle and the SID.

When having received the fully-open/restore instruction, the limiting controlling circuitry 20, at first, stores position information (restoration position information) indicating the restoration positions into the storage circuitry 24, according to the fully-open/restore instruction. Further, the limiting controlling circuitry 20 moves the positions of the limiting blades to the positions corresponding to the maximum opening degree. After that, the limiting controlling circuitry 20 obtains the restoration position information from the storage circuitry 24. Subsequently, the limiting controlling circuitry 20 moves the positions of the limiting blades to the restoration positions indicated by the restoration position information.

In other words, when a change occurred in the C-arm information, the limiting blades are moved from the restoration positions to the positions corresponding to the maximum opening degree and are subsequently moved to return from the positions corresponding to the maximum opening degree to the restoration positions. The opening degree of the opening part of the X-ray limiting device 13 observed at the time of the change in the C-arm information (the clinical angle and the SID) is an example of the first opening degree. Further, the maximum opening degree is an example of the second opening degree.

In this situation, the background image managing function 215 obtains X-ray image data based on the projection data acquired while the opening part of the X-ray limiting device 13 is fully open (in the state with the maximum opening degree) according to the fully-open/restore instruction, as background image data (fully-open background image data) from the storage circuitry 24. After that, the background image managing function 215 transmits the obtained fully-open background image data to the combining function 216.

Subsequently, every time X-ray image data transmitted thereto from the image generating function 214 is received, the combining function 216 transmits combined image data obtained by combining the X-ray image data with the fully-open background image data, to the controlling function 213. For example, the combining function 216 generates the combined image data by combining the X-ray image data corresponding to the opening degree of the opening part of the X-ray limiting device 13 observed at the time of the change in the C-arm information (the clinical angle and the SID), with the fully-open background image data corresponding to the maximum opening degree. The combining method is the same as the method described in the first embodiment.

Further, for example, as illustrated in FIG. 9, when the input interface 22 receives a change to be made to a Field Of View (FOV) from the user, the controlling function 213 transmits the post-change FOV to the background image managing function 215. In this situation, for example, the FOV is information indicating the range of detecting elements used in the image taking process (i.e., the detecting elements radiated with the X-rays), among the plurality of detecting elements arranged in the matrix formation in the X-ray detector 16.

When having received the post-change FOV, the background image managing function 215 transmits a fully-open/restore instruction to the limiting controlling circuitry 20. In this situation, the fully-open/restore instruction is an instruction indicating that the positions of the limiting blades should be moved so that the opening part of the X-ray limiting device 13 is fully open and the opening degree is at a maximum, and subsequently, that the positions of the limiting blades should be moved so that the shape, the size, and the position of the opening part correspond to the post-change FOV.

When having received the fully-open/restore instruction, the limiting controlling circuitry 20, at first, moves the positions of the limiting blades so that the opening part of the X-ray limiting device 13 is fully open and the opening degree is equal to the maximum opening degree, according to the fully-open/restore instruction. After that, the limiting controlling circuitry 20 moves the positions of the limiting blades so that the shape, the size, and the position of the opening part correspond to the post-change FOV. In other words, when a change occurred to the FOV, the limiting blades are moved to the positions corresponding to the maximum opening degree larger than the opening degree corresponding to the FOV and are subsequently moved to return from the positions corresponding to the maximum opening degree to the positions that correspond to the opening degree corresponding to the FOV. The opening degree corresponding to the FOV is an example of the first opening degree.

In this situation, the background image managing function 215 obtains the fully-open background image data and transmits the obtained fully-open background image data to the combining function 216.

After that, every time X-ray image data transmitted thereto from the image generating function 214 is received, the combining function 216 transmits combined image data obtained by combining the X-ray image data with the fully-open background image data, to the controlling function 213. For example, the combining function 216 generates the combined image data by combining the X-ray image data corresponding to the FOV with the fully-open background image data corresponding to the maximum opening degree. The combining method is the same as the method described in the first embodiment.

In the first modification example, the background image managing function 215 may transmit the fully-open/restore instruction to the limiting controlling circuitry 20, according to an instruction from the user via the input interface 22.

The first modification example of the first embodiment has thus been explained. Even when a change occurred in the C-arm information or the FOV, the X-ray diagnosis apparatus 100 according to the first modification example is able to continue the partial fluoroscopy by updating the background image data, without requiring the user to set a region of interest. Accordingly, by using the X-ray diagnosis apparatus 100 according to the first modification example, it is possible to improve operability in the implementation of the partial fluoroscopy.

Second Modification Example of First Embodiment

In the first embodiment above, the example was explained in which, during the partial fluoroscopy, the background image data is updated by discarding the background image data that has so far been saved and newly obtaining background image data; however, some users may not like the configuration where the background image displayed on the display 23 is updated during the partial fluoroscopy. For this reason, the X-ray diagnosis apparatus 100 may be configured not to update the background image during the partial fluoroscopy. Thus, this embodiment will be explained as a second modification example of the first embodiment. The explanations of the processes that are the same as those in the first embodiment and the modification examples of the first embodiment will be omitted.

For example, a situation where the partial fluoroscopy is performed multiple times will be explained. At each time when the partial fluoroscopy is performed, the combining function 216 performs the process (a combined image data generating process) of sequentially generating the combined image data once. Accordingly, when the partial fluoroscopy is performed multiple times, the combining function 216 performs the combined image data generating process multiple times.

Further, in the second modification example, during the partial fluoroscopy, the background image managing function 215 does not update the background image data. In other words, during the partial fluoroscopy, the background image managing function 215 does not perform the process of updating the background data where the saved background image data is discarded and background image data is newly obtained.

Further, in the second modification example, the controlling function 213 has a Last Image Hold (LIH) function to save the most recent combined image data, background image data, and the like and is therefore capable of causing the display 23 to display the most recent combined image data until the next fluoroscopy is performed.

In the second modification example, among the multiple times when the combined image data generating process is performed, the background image managing function 215 performs the processes described below, at least in the time period between one combined image data generating process (a first process) and another combined image data generating process (a second process) performed subsequent to the one combined image data generating process. For example, the background image managing function 215 judges whether the opening degree (a third opening degree) of the opening part of the X-ray limiting device 13 observed at the time of acquiring the X-ray image data (the abovementioned first X-ray image data) used for generating the combined image data generated at last in the first process is equal to or larger than the opening degree (a fourth opening degree) of the opening part observed at the time of acquiring the background image data used for generating the combined image data in the first process.

When the third opening degree is equal to or larger than the fourth opening degree, the background image managing function 215 transmits, before the second process is performed, the X-ray image data used for generating the combined image data generated at last in the first process to the combining function 216, so that the transmitted X-ray image data is to be used as the background image data in the second process. Accordingly, the combining function 216 sequentially generates combined image data by using the X-ray image data used for generating the combined image data generated at last in the first process, as the background image data in the second process.

Further, when the third opening degree is equal to or larger than the fourth opening degree, the background image managing function 215 further deletes the background image data used for generating the combined image data in the first process, from the storage circuitry 24.

The X-ray diagnosis apparatus 100 according to the second modification example of the first embodiment has thus been explained. The X-ray diagnosis apparatus 100 according to the second modification example does not update the background image displayed on the display 23 during the partial fluoroscopy. Accordingly, by using the X-ray diagnosis apparatus 100 according to the second modification example, it is possible to realize appropriate display according to preference of the user.

In the second modification example, similarly to the first embodiment, the background image managing function 215 may discard the background image data when a change occurred in the C-arm information during the implementation of the partial fluoroscopy. Further, the controlling function 213 may control the entirety of the X-ray diagnosis apparatus 100 so that the entire-area fluoroscopy is implemented.

Second Embodiment

In the first embodiment and the modification examples described above, the example was explained in which the display 23 displays the combined images in a real-time manner, as the partial fluoroscopic images. However, the display 23 may display difference images in a real-time manner, as partial fluoroscopic images. Thus, this embodiment will be explained as a second embodiment. The following will describe differences from the above embodiments and modification examples. Some of the configurations that are the same as above will be referred to by using the same reference characters, and the explanations thereof may be omitted. Also, the explanations of the same processes as above may be omitted.

Figure 10:
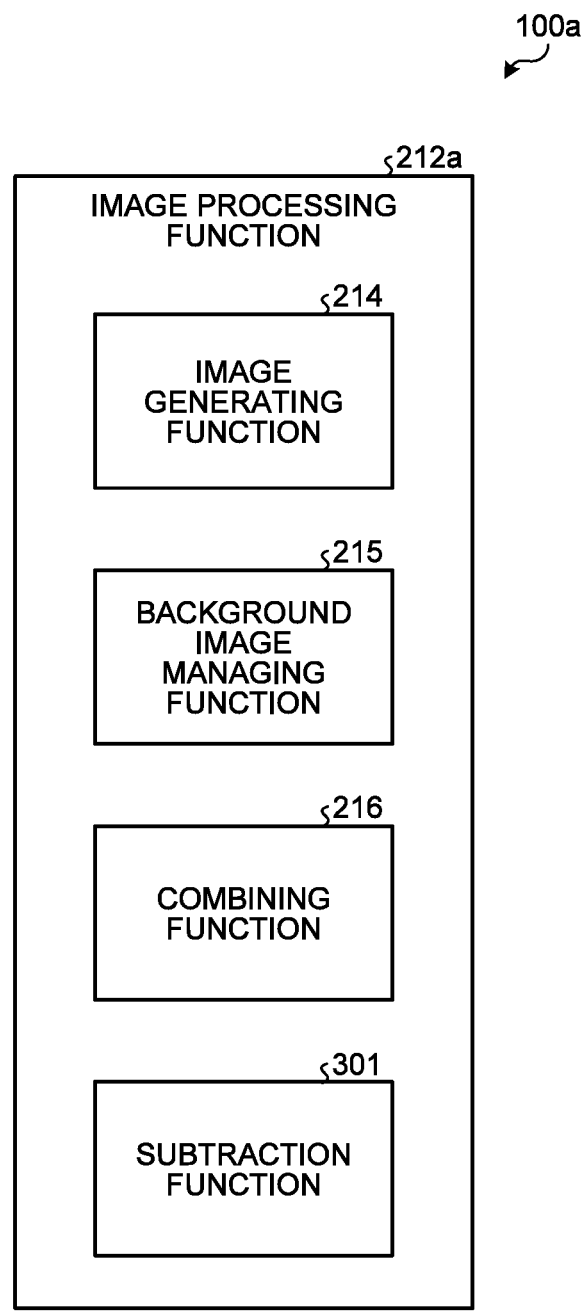
FIG. 10 is a diagram illustrating an exemplary configuration of an image processing function included in an X-ray diagnosis apparatus according to a second embodiment.

FIG. 10 is a diagram illustrating an exemplary configuration of an image processing function 212a included in an X-ray diagnosis apparatus 100a according to the second embodiment. The X-ray diagnosis apparatus 100a according to the second embodiment is different from the X-ray diagnosis apparatus 100 according to the first embodiment illustrated in FIG. 1 for including the image processing function 212a illustrated in FIG. 10, in place of the image processing function 212 illustrated in FIG. 2.

In addition to the image generating function 214, the background image managing function 215, and the combining function 216, the image processing function 212a includes a subtraction function 301. In the second embodiment, the combining function 216 and the subtraction function 301 serve as an example of a second generating unit. The subtraction function 301 will be explained later.

In the second embodiment, in the partial fluoroscopy, the user selects one of the following two modes: a mode (a combined image mode) in which the display 23 sequentially displays the abovementioned combined images (e.g., the combined image 36 illustrated in FIG. 7A) as fluoroscopic images; and another mode (a difference image mode) in which the display 23 sequentially displays difference images as fluoroscopic images.

When the combined image mode is selected, the same processes as those described in the first embodiment are performed, so that the display 23 sequentially displays the combined images. In contrast, when the difference image mode is selected, the display 23 sequentially displays the difference images. Next, an example of processes performed by the X-ray diagnosis apparatus 100a according to the second embodiment when the difference image mode is selected will be explained, with reference to FIGS. 11 and 12.

Figure 11:
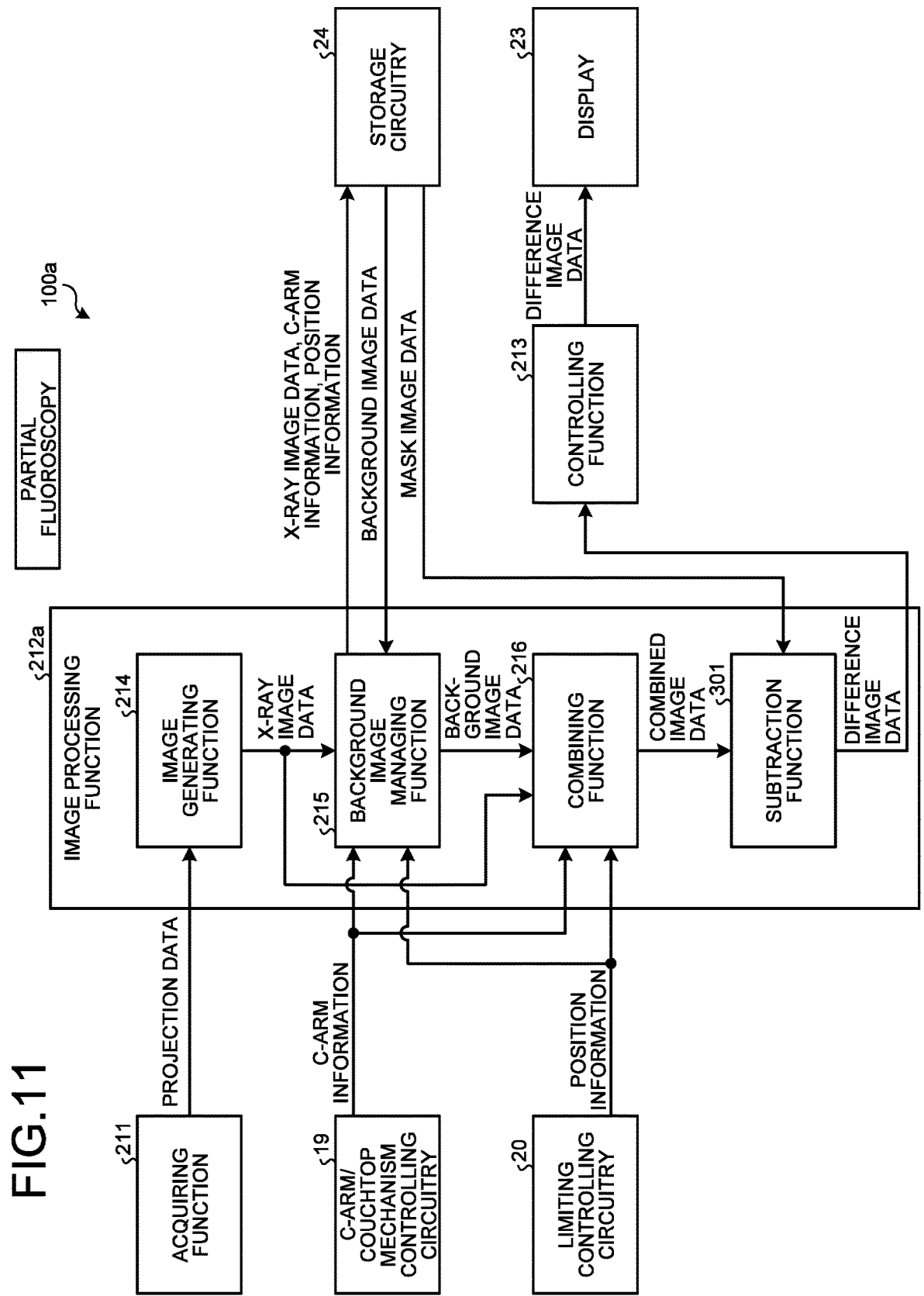
FIG. 11 is a chart for explaining an example of processes performed by the X-ray diagnosis apparatus according to the second embodiment.

FIG. 11 is a chart for explaining the example of the processes performed by the X-ray diagnosis apparatus 100a according to the second embodiment. FIG. 11 illustrates the example of the processes performed by the X-ray diagnosis apparatus 100a when the difference image mode is selected.

As illustrated in FIG. 11, every time one frame of combined image data is generated, the combining function 216 transmits the generated combined image data to the subtraction function 301. Every time one frame of combined image data is received, the subtraction function 301 generates one frame of difference image data by using the received combined image data and mask image data.

Figure 12:
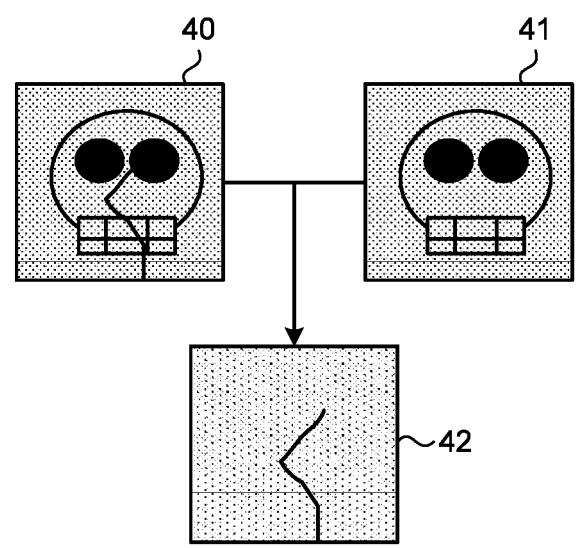
FIG. 12 is a drawing for explaining an example of a method for generating difference image data according to the second embodiment.

Next, an example of a method for generating the difference image data will be explained. FIG. 12 is a drawing for explaining the example of the method for generating the difference image data according to the second embodiment.

For example, the subtraction function 301 obtains mask image data 41 from the storage circuitry 24. After that, as illustrated in FIG. 12, the subtraction function 301 generates difference image data 42 by calculating the difference between combined image data 40 and the mask image data 41. In other words, the subtraction function 301 generates the difference image data 42 by subtracting the mask image data 41 from the combined image data 40. In this manner, the subtraction function 301 sequentially generates the difference image data 42 obtained by combining the combined image data 40 with the mask image data 41. The mask image data 41 is an example of the third X-ray image data. The difference image data 42 is an example of the second combined image data.

In this situation, the mask image data 41 is stored in the storage circuitry 24 before the partial fluoroscopy is implemented. For example, the mask image data 41 is image data obtained by the image generating function 214 by calculating an arithmetic mean of a plurality of pieces of X-ray image data generated on the basis of projection data acquired while no medical device such as a catheter is inserted in the patient P. Accordingly, no medical device is rendered in the mask image data 41, although the surrounding tissues (the background) such as bones of the patient P are rendered therein. Thus, the medical device is clearly rendered in the difference image data 42 obtained by calculating the difference between the mask image data 41 and the combined image data 40 rendering the background and the medical device. The medical device is an example of the device.

Further, every time one frame of the difference image data 42 is generated, the subtraction function 301 transmits the generated difference image data 42 to the controlling function 213.

Every time one frame of the difference image data 42 is received, the controlling function 213 causes the display 23 to display a difference image (a partial fluoroscopic image) represented by the received difference image data (the partial fluoroscopic image data) 42. Accordingly, the display 23 sequentially displays partial fluoroscopic images obtained by the partial fluoroscopy. In other words, the display 23 is configured to display the partial fluoroscopic images in a real-time manner.

The X-ray diagnosis apparatus 100a according to the second embodiment has thus been explained. In the second embodiment, the combined image data 40 renders the background and the medical device. Further, of the background and the medical device, the mask image data 41 renders the background. Further, the subtraction function 301 sequentially generates the difference image data 42 indicating the difference between the combined image data 40 and the mask image data 41. By using the X-ray diagnosis apparatus 100a according to the second embodiment, it is possible to improve operability in the implementation of the partial fluoroscopy, similarly to the first embodiment.

Third Embodiment

In the embodiments and the modification examples described above, the example was explained in which the display 23 displays the abovementioned combined images in a real-time manner as the partial fluoroscopic images. However, the display 23 may display other combined images in a real-time manner as partial fluoroscopic images. Thus, this embodiment will be explained as a third embodiment. The following will describe differences from the above embodiments and modification examples. Some of the configurations that are the same as above will be referred to by using the same reference characters, and the explanations thereof may be omitted. Also, the explanations of the same processes as above may be omitted.

Figure 13:
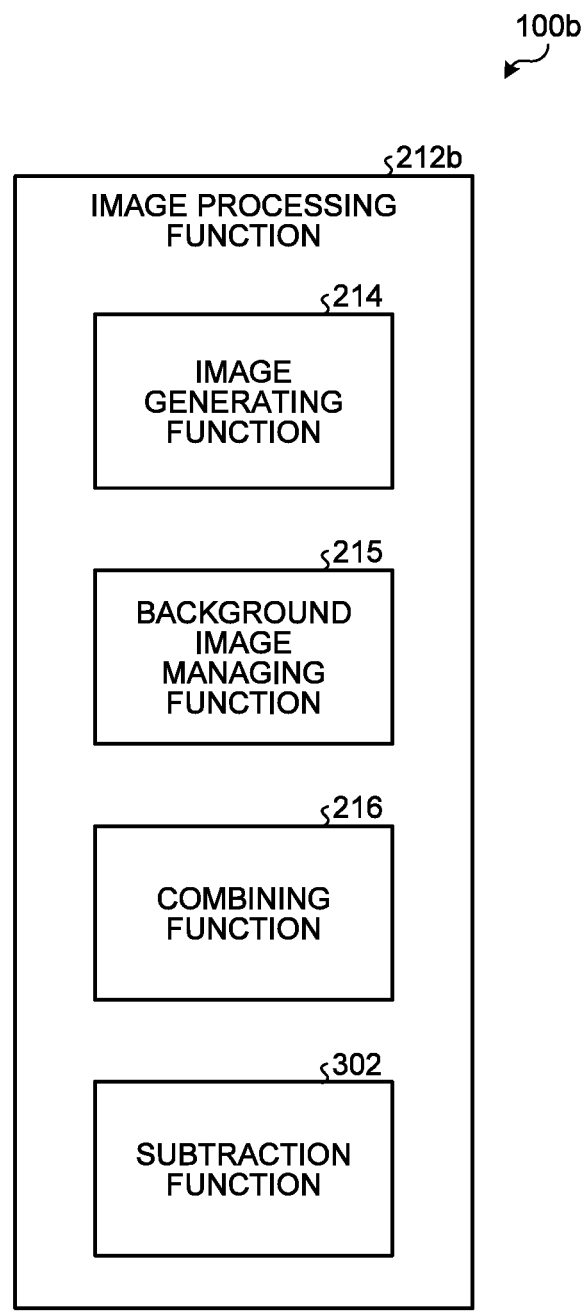
FIG. 13 is a diagram illustrating an exemplary configuration of an image processing function included in an X-ray diagnosis apparatus according to a third embodiment.

FIG. 13 is a diagram illustrating an exemplary configuration of an image processing function 212b included in an X-ray diagnosis apparatus 100b according to the third embodiment. The X-ray diagnosis apparatus 100b according to the third embodiment is different from the X-ray diagnosis apparatus 100 according to the first embodiment illustrated in FIG. 1, for including the image processing function 212b illustrated in FIG. 13 in place of the image processing function 212 illustrated in FIG. 2.

In addition to the image generating function 214, the background image managing function 215, and the combining function 216, the image processing function 212b includes a subtraction function 302. In the third embodiment, the combining function 216 and the subtraction function 302 serve as an example of a second generating unit. The subtraction function 302 will be explained later.

In the third embodiment, in the partial fluoroscopy, the user selects one of the following two modes: the combined image mode in which the display 23 sequentially displays the abovementioned combined images (e.g., the combined image 36 illustrated in FIG. 7A) as fluoroscopic images; and another mode in which the display 23 sequentially displays other combined images as fluoroscopic images. In the following sections, the "combined image mode" explained in the second embodiment will be referred to as a "first combined image mode", whereas the mode in which the other combined images are sequentially displayed will be referred to as a "second combined image mode".

For example, when the first combined image mode is selected, the same processes as those in the second embodiment are performed, so that the display 23 sequentially displays the combined images. In contrast, when the second combined image mode is selected, the display 23 sequentially displays the other combined images. Next, an example of processes performed by the X-ray diagnosis apparatus 100b according to the third embodiment when the second combined image mode is selected will be explained, with reference to FIG. 14.

Figure 14:
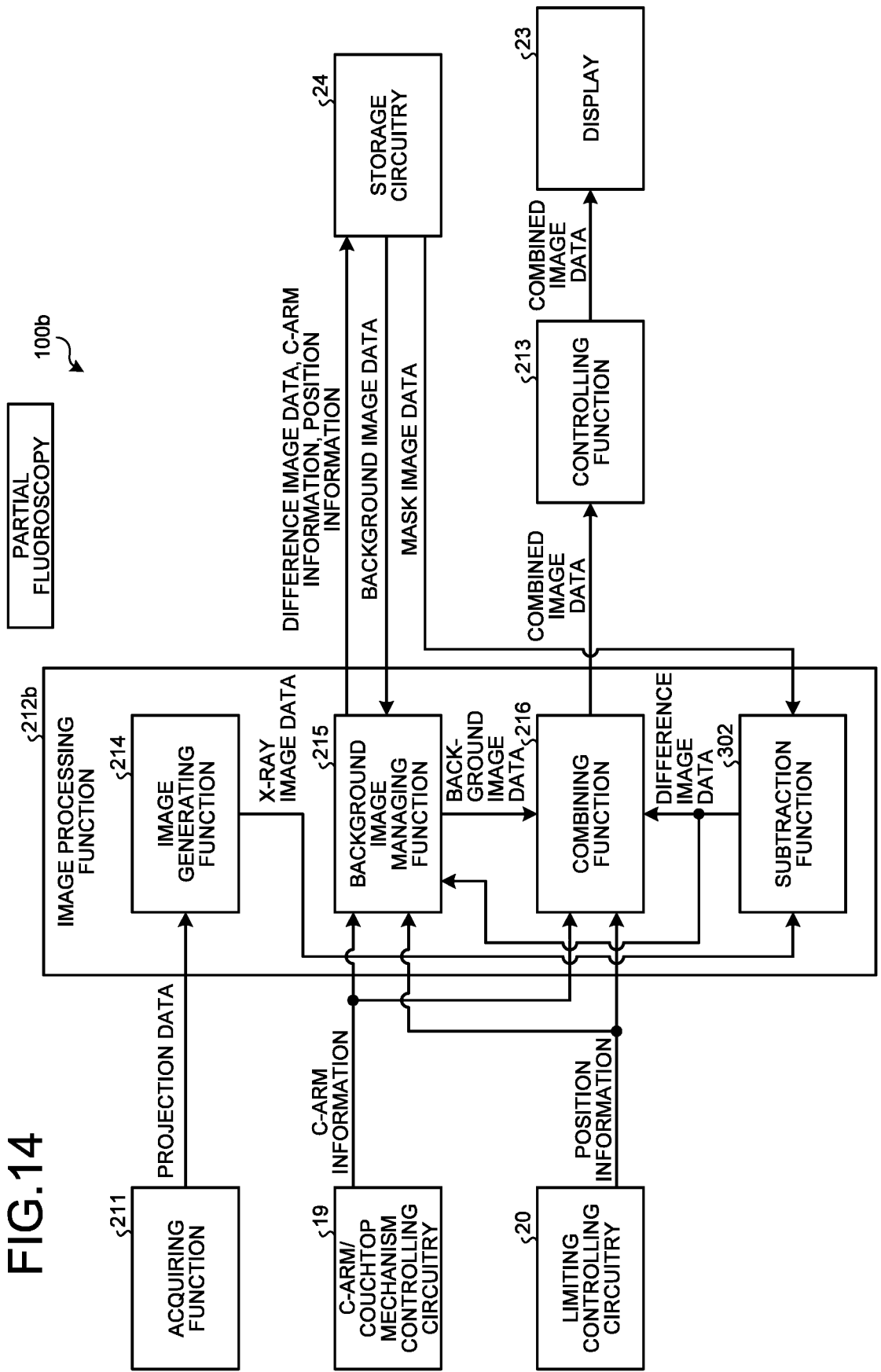
FIG. 14 is a chart for explaining an example of processes performed by the X-ray diagnosis apparatus according to the third embodiment.

FIG. 14 is a chart for explaining the example of the processes performed by the X-ray diagnosis apparatus 100b according to the third embodiment. FIG. 14 illustrates the example of the processes performed by the X-ray diagnosis apparatus 100b when the second combined image mode is selected.

As illustrated in FIG. 14, every time one frame of X-ray image data (real-time image data) is generated, the image generating function 214 transmits the generated X-ray image data to the subtraction function 302. Every time one frame of X-ray image data is received, the subtraction function 302 generates one frame of difference image data by using the received X-ray image data and mask image data.

Next, an example of a method for generating the difference image data in the third embodiment will be explained. For example, the subtraction function 302 obtains the mask image data from the storage circuitry 24. Further, as illustrated in FIG. 14, the subtraction function 302 generates the difference image data by calculating the difference between the received X-ray image data and the mask image data. In other words, the subtraction function 302 generates the difference image data by subtracting the mask image data from the X-ray image data. In this manner, the subtraction function 302 sequentially generates the difference image data obtained by combining the X-ray image data with the mask image data. In this situation, the X-ray image data is an example of the first X-ray image data. Further, the mask image data in the third embodiment is an example of the third X-ray image data. The difference image data in the third embodiment is an example of the third combined image data.

In this situation, the mask image data in the third embodiment is the same or similar data as the mask image data 41 in the second embodiment and is stored in the storage circuitry 24 before the partial fluoroscopy is implemented. Thus, the medical device is clearly rendered in the difference image data obtained by calculating the difference between the mask image data in the third embodiment and the X-ray image data (the real-time image data) rendering the background and the medical device.

Further, every time one frame of difference image data is generated, the subtraction function 302 transmits the generated difference image data to the background image managing function 215 and the combining function 216.

In this situation, the background image managing function 215 in the third embodiment performs the following processes by using the same method as the method used by the abovementioned background image managing function 215 in the first embodiment by which the X-ray image data (the real-time image data), the C-arm information, and the position information are stored into the storage circuitry 24 so as to be kept in correspondence with one another and, when a change occurred in the positions of the limiting blades, the background image data to be used in the partial fluoroscopy is obtained from the storage circuitry 24.

For example, as illustrated in FIG. 14, every time difference image data transmitted thereto from the subtraction function 302 is received, the background image managing function 215 according to the third embodiment stores the received difference image data, the C-arm information, and the position information, into the storage circuitry 24 so as to be kept in correspondence with one another. After that, when a change occurred in the positions of the limiting blades, the background image managing function 215 according to the third embodiment obtains the difference image data to be used as the background image data in the partial fluoroscopy, from the storage circuitry 24. Subsequently, the background image managing function 215 according to the third embodiment transmits the obtained background image data (the difference image data) to the combining function 216. The background image data in the third embodiment is an example of the fourth combined image data.

In this situation, as explained above, every time one frame of X-ray image data is received, the combining function 216 according to the first embodiment generates one frame of combined image data (the partial fluoroscopic image data) by combining the most recent background image data with the received X-ray image data, while using the C-arm information and the position information corresponding to the X-ray image data.

By performing the same processes as those performed by the combining function 216 according to the first embodiment described above, every time one frame of difference image data is received, the combining function 216 according to the third embodiment generates one frame of combined image data (partial fluoroscopic image data) by combining the most recent background image data with the received difference image data, while using the C-arm information and the position information corresponding to the difference image data. The combined image data generated by the combining function 216 according to the third embodiment is an example of the fifth combined image data.

Further, every time one frame of combined image data is generated, the combining function 216 transmits the generated combined image data to the controlling function 213.

Every time one frame of combined image data is received, the controlling function 213 causes the display 23 to display a combined image (a partial fluoroscopic image) represented by the received combined image data. Accordingly, the display 23 sequentially displays partial fluoroscopic images obtained by the partial fluoroscopy. In other words, the display 23 is configured to display the partial fluoroscopic images in a real-time manner.

The X-ray diagnosis apparatus 100b according to the third embodiment has thus been explained.

In the third embodiment, the X-ray image data generated during the move of the limiting blades renders the background and the device. Similarly, the X-ray image data generated prior to the move of the limiting blades also renders the background and the medical device. In contrast, of the background and the medical device, the mask image data renders the background.

Further, the subtraction function 302 is configured to sequentially generate the difference image data indicating the difference between the X-ray image data generated during the move of the limiting blades and the mask image data. Further, the subtraction function 302 is configured to generate the background image data indicating the difference between the X-ray image data generated prior to the move of the limiting blades and the mask image data. After that, the combining function 216 is configured to sequentially generate the combined image data obtained by combining the difference image data with the background image data.

By using the X-ray diagnosis apparatus 100b according to the third embodiment, it is possible to improve operability in the implementation of the partial fluoroscopy, similarly to the first embodiment and the second embodiment.

Figure 15:
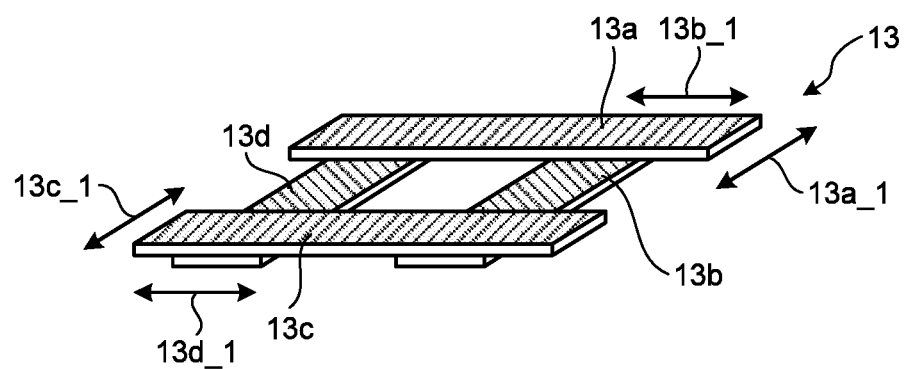
FIG. 15 is a drawing illustrating an exemplary configuration of an X-ray limiting device used in embodiments and modification examples.

Next, an exemplary configuration of the X-ray limiting device 13 used in the embodiments and the modification examples described above will be explained. FIG. 15 is a drawing illustrating the exemplary configuration of the X-ray limiting device 13 used in the embodiments and the modification examples.

As illustrated in FIG. 15, the X-ray limiting device 13 includes four (a plurality of) limiting blades 13a to 13d that are movable. The limiting blades 13a to 13d are formed by using a material such as metal that is able to restrict the radiation range of the X-rays. For example, the limiting blades 13a to 13d are plate-like members. The limiting blades 13a to 13d each have a rectangular shape in a top view.

The limiting blade 13a is movable within a predetermined range in the width direction of the limiting blade 13a (the direction indicated by the arrow 13a_1). Similarly, each of the limiting blades 13b, 13c, and 13d is movable within a predetermined range in the width direction of the limiting blades 13b, 13c, and 13d (the direction indicated by each of the arrows 13b_1, 13c_1, and 13d_1).

The user is able to individually move each of the limiting blades 13a to 13d by operating the input interface 43.

The term "processor" used in the above explanation denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors realize the functions by reading and executing the programs saved in the storage circuitry 24. In this situation, instead of saving the programs in the storage circuitry 24, it is also acceptable to directly incorporate the programs in the circuitries of the processors. In that situation, the processors realize the functions thereof by reading and executing the programs incorporated in the circuitries thereof. The processors in the present embodiments do not each necessarily have to be structured as a single circuitry. It is also acceptable to structure one processor by combining together a plurality of independent circuitries so as to realize the functions thereof.

In this regard, a medical image processing computer program (hereinafter, "medical image processing program") executed by the one or more processors is provided as being incorporated in a Read-Only Memory (ROM), a storage unit, or the like. The medical image processing program may be provided as being stored in a computer-readable storage medium such as a Compact Disk Read-Only Memory (CD-ROM), a Flexible Disk (FD), a Compact Disk Recordable (CD-R), a Digital Versatile Disk (DVD), or the like, in a file in an installable format or in an executable format for the devices. Further, the medical image processing program may be stored in a computer connected to a network such as the Internet, so as to be provided or distributed as being downloaded via the network. For example, the medical image processing program is structured with modules including the functional units described below. In the actual hardware, as a result of a CPU reading and executing the program from a storage medium such as a ROM, the modules are loaded into a main storage device so as to be generated in the main storage device.

Further, the constituent elements of the apparatuses and the devices illustrated in the drawings in the above embodiments are based on functional concepts. Thus, it is not necessary to physically configure the constituent elements as indicated in the drawings. In other words, specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program analyzed and executed by the CPU or may be realized as hardware using wired logic.

According to at least one aspect of the embodiments and the modification examples described above, it is possible to improve operability in the implementation of the partial fluoroscopy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus comprising:
   an X-ray tube configured to generate X-rays;
   an X-ray detector configured to detect X-rays emitted from the X-ray tube;
   storage circuitry configured to store therein X-ray image data sequentially generated on a basis of a detection result obtained by the X-ray detector;
   an X-ray limiting device including a plurality of movable X-ray blocking members and being configured to restrict a range radiated with the X-rays emitted from the X-ray tube;
   an input interface configured to receive an operation to move at least one of the X-ray blocking members; and
   processing circuitry configured:
   to sequentially generate the X-ray image data based on the detection result obtained by the X-ray detector;
   to specify, based on position information indicating positions of the X-ray blocking members during the move, a radiation region of the X-rays in each piece of X-ray image data generated during the move of the at least one of the X-ray blocking members that is moved by the X-ray limiting device on a basis of the operation received by the input interface, each piece of the X-ray image data being generated based on a detection result obtained by the X-ray detector during the move;
   to sequentially generate, during the move of the at least one of the X-ray blocking members, first combined image data by using the radiation region, by combining first X-ray image data generated during the move of the at least one of the X-ray blocking members, with second X-ray image data generated prior to the move of the at least one of the X-ray blocking members and stored in the storage circuitry; and
   to cause a display to sequentially display combined images represented by the first combined image data.

2. The X-ray diagnosis apparatus according to claim 1, wherein
   the X-ray limiting device includes four of the X-ray blocking members, and
   the input interface receives the operation to move an opposing pair of X-ray blocking members among the four X-ray blocking members.

3. The X-ray diagnosis apparatus according to claim 1, wherein the processing circuitry generates the first combined image data by combining the first X-ray image data with the second X-ray image data corresponding to a largest opening degree of the X-ray blocking members among such a plurality of pieces of the X-ray image data generated under a same geometric condition as a geometric condition related to an image taking process performed for generating the first X-ray image data.

4. The X-ray diagnosis apparatus according to claim 3, wherein, when the plurality of pieces of the X-ray image data include two or more pieces of second X-ray image data corresponding to the largest opening degree of the X-ray blocking members, the processing circuitry generates the first combined image data by combining the first X-ray image data with the most recent second X-ray image data among the two or more pieces of second X-ray image data corresponding to the largest opening degree.

5. The X-ray diagnosis apparatus according to claim 1, wherein
   when a change occurred in a geometric condition related to an image taking process, the at least one of the X-ray blocking members is moved from a position corresponding to a first opening degree observed at a time of the change in the geometric condition to a position corresponding to a second opening degree larger than the first opening degree and is subsequently moved to return from the position corresponding to the second opening degree to the position corresponding to the first opening degree, and the processing circuitry generates the first combined image data by combining the first X-ray image data corresponding to the first opening degree with the second X-ray image data corresponding to the second opening degree.

6. The X-ray diagnosis apparatus according to claim 1, wherein when a change occurred in a Field Of View (FOV), the at least one of the X-ray blocking members is moved to a position corresponding to a second opening degree larger than a first opening degree corresponding to the FOV and is subsequently moved to return from the position corresponding to the second opening degree to a position corresponding to the first opening degree, and the processing circuitry generates the first combined image data by combining the first X-ray image data corresponding to the first opening degree with the second X-ray image data corresponding to the second opening degree.

7. The X-ray diagnosis apparatus according to claim 1, wherein the processing circuitry processes by performing a process of sequentially generating the first combined image data multiple times, and among the processes, at least between a first process and a second process performed subsequent to the first process, when an opening degree of the X-ray blocking members corresponding to the first X-ray image data used for generating the first combined image data generated at last in the first process is equal to or larger than an opening degree of the X-ray blocking members corresponding to the second X-ray image data used for generating the first combined image data in the first process, the processing circuitry generates the first combined image data by using the first X-ray image data used for generating the first combined image data generated at last in the first process, as second image data in the second process.

8. The X-ray diagnosis apparatus according to claim 7, wherein, among the processes, at least between the first process and the second process, when the opening degree of the X-ray blocking members corresponding to the first X-ray image data used for generating the first combined image data generated at last in the first process is equal to or larger than the opening degree of the X-ray blocking members corresponding to the second X-ray image data used for generating the first combined image data in the first process, the processing circuitry deletes, from the storage circuitry, the second X-ray image data used for generating the first combined image data in the first process.

9. The X-ray diagnosis apparatus according to claim 1, wherein the processing circuitry sequentially generates second combined image data by combining the first combined image data with third X-ray image data.

10. The X-ray diagnosis apparatus according to claim 9, wherein the first combined image data renders a background and a device, of the background and the device, the third X-ray image data renders the background, and the processing circuitry sequentially generates difference image data indicating a difference between the first combined image data and the third X-ray image data, as the second combined image data.

11. The X-ray diagnosis apparatus according to claim 1, wherein the processing circuitry sequentially generates fourth combined image data by combining second combined image data with third combined image data, the second combined image data being obtained by combining the first X-ray image data generated during the move of the at least one of the X-ray blocking members with third X-ray image data stored in the storage circuitry; and the third combined image data being obtained by combining the second X-ray image data generated prior to the move of the at least one of the X-ray blocking members with the third X-ray image data.

12. The X-ray diagnosis apparatus according to claim 11, wherein the first X-ray image data renders a background and a device, of the background and the device, the third X-ray image data renders the background, the processing circuitry sequentially generates difference image data indicating a difference between the first X-ray image data generated during the move of the at least one of the X-ray blocking members and the third X-ray image data, as the third combined image data, the processing circuitry generates difference image data indicating a difference between the second X-ray image data generated prior to the move of the at least one of the X-ray blocking members and the third X-ray image data, as fifth combined image data, and the processing circuitry generates the fourth combined image data by combining the second combined image data with the third and the fifth combined image data.

13. An X-ray diagnosis apparatus comprising:

an X-ray tube configured to generate X-rays;

an X-ray detector configured to detect X-rays emitted from the X-ray tube;

storage circuitry configured to store therein X-ray image data sequentially generated on a basis of a detection result obtained by the X-ray detector;

an X-ray limiting device including a plurality of movable X-ray blocking members and being configured to restrict a range radiated with the X-rays emitted from the X-ray tube;

an input interface configured to receive an operation to move individually one or more of the plurality of X-ray blocking members; and processing circuitry configured:

to sequentially generate the X-ray image data based on the detection result obtained by the X-ray detector;

to generate first combined image data by combining first X-ray image data related to a region of interest defined by the one or more of the plurality of X-ray blocking members individually moved on a basis of the operation received by the input interface, with second X-ray image data generated prior to the move of the one or more of the plurality of X-ray blocking members, the first X-ray image data being generated during the move of the one or more of the plurality of the X-ray blocking members; and to cause a display to display a combined image represented by the first combined image data.

14. An image processing method comprising:
sequentially generating X-ray image data based on a detection result obtained by an X-ray detector configured to detect X-rays emitted from an X-ray tube;
storing the generated X-ray image data into storage circuitry;
specifying a radiation region of the X-rays in each piece of X-ray image data generated during a move of a movable X-ray blocking member of a plurality of movable X-ray blocking members that are included in an X-ray limiting device and is moved by the X-ray limiting device configured to restrict a range radiated with the X-rays emitted from the X-ray tube based on position information indicating a position of the X-ray blocking member during the move, on a basis of an operation received by an input interface and to move the X-ray blocking member, each piece of the X-ray image data being generated based on a detection result obtained by the X-ray detector during the move;
sequentially generating, during the move of the X-ray blocking member, first combined image data by using the radiation region, by combining first X-ray image data generated during the move of the X-ray blocking member, with second X-ray image data generated prior to the move of the X-ray blocking member and stored in the storage circuitry; and
causing a display to sequentially display combined images represented by the first combined image data.

15. The image processing method according to claim 14, comprising generating the first combined image data by combining the first X-ray image data with the second X-ray image data corresponding to a largest opening degree of the X-ray blocking members among such a plurality of pieces of the X-ray image data generated under a same geometric condition as a geometric condition related to an image taking process performed for generating the first X-ray image data.

16. The image processing method according to claim 15, comprising, when the plurality of pieces of the X-ray image data include two or more pieces of second X-ray image data corresponding to the largest opening degree of the X-ray blocking members, generating the first combined image data by combining the first X-ray image data with the most recent second X-ray image data among the two or more pieces of second X-ray image data corresponding to the largest opening degree.

17. The image processing method according to claim 14, comprising:
at least one of:
when a change occurred in a geometric condition related to an image taking process, moving the X-ray blocking member from a position corresponding to a first opening degree observed at a time of the change in the geometric condition to a position corresponding to a second opening degree larger than the first opening degree and subsequently moving the X-ray blocking member to return from the position corresponding to the second opening degree to the position corresponding to the first opening degree, and
when a change occurred in a Field Of View (FOV), moving the X-ray blocking member to a position corresponding to a second opening degree larger than a first opening degree corresponding to the FOV and subsequently moving the X-ray blocking member to return from the position corresponding to the second opening degree to a position corresponding to the first opening degree; and
generating the first combined image data by combining the first X-ray image data corresponding to the first opening degree with the second X-ray image data corresponding to the second opening degree.

18. The image processing method according to claim 14, comprising:
performing a process of sequentially generating the first combined image data multiple times;
among the processes, at least between a first process and a second process performed subsequent to the first process, when an opening degree of the X-ray blocking members corresponding to the first X-ray image data used for generating the first combined image data generated at last in the first process is equal to or larger than an opening degree of the X-ray blocking members corresponding to the second X-ray image data used for generating the first combined image data in the first process, generating the first combined image data by using the first X-ray image data used for generating the first combined image data generated at last in the first process, as second X-ray image data in the second process; and
among the processes, at least between the first process and the second process, when the opening degree of the X-ray blocking members corresponding to the first X-ray image data used for generating the first combined image data generated at last in the first process is equal to or larger than the opening degree of the X-ray blocking members corresponding to the second X-ray image data used for generating the first combined image data in the first process, deleting, from the storage circuitry, the second X-ray image data used for generating the first combined image data in the first process.

19. The image processing method according to claim 14, comprising:
generating second combined image data by combining the first combined image data with third X-ray image data, wherein
the first combined image data renders a background and a device, and
of the background and the device, the third X-ray image data renders the background, and
sequentially generating difference image data indicating a difference between the first combined image data and the third X-ray image data, as the second combined image data.

20. The image processing method according to claim 14, comprising:
sequentially generating fourth combined image data by combining second combined image data with third combined image data, the second combined image data being obtained by combining the first X-ray image data generated during the move of the X-ray blocking member with third X-ray image data stored in the storage circuitry; and the third combined image data being obtained by combining the second X-ray image data generated prior to the move of the X-ray blocking member with the third X-ray image data, wherein
the first X-ray image data renders a background and a device, and
of the background and the device, the third X-ray image data renders the background;
sequentially generating difference image data indicating a difference between the first X-ray image data generated during the move of the X-ray blocking member and the third X-ray image data, as the third combined image data;

generating difference image data indicating a difference between the second X-ray image data generated prior to the move of the X-ray blocking member and the third X-ray image data, as fifth combined image data; and generating the fourth combined image data by combining the second combined image data with the third and the fifth combined image data.

* * * * *